United States Patent
Henriksen

(10) Patent No.: US 6,770,620 B2
(45) Date of Patent: Aug. 3, 2004

(54) USE OF GLP FOR THE TREATMENT, PREVENTION, DIAGNOSIS, AND PROGNOSIS OF BONE-RELATED AND NUTRITION-RELATED DISORDERS

(75) Inventor: Dennis Bang Henriksen, Alleroed (DK)

(73) Assignee: Sanos Bioscience A/S, Herlev (DK)

( * ) Notice: Subject to any disclaimer, the term of this patent is extended or adjusted under 35 U.S.C. 154(b) by 0 days.

(21) Appl. No.: 09/954,304

(22) Filed: Sep. 17, 2001

(65) Prior Publication Data

US 2002/0037836 A1 Mar. 28, 2002

(30) Foreign Application Priority Data

Sep. 18, 2000 (GB) .............................................. 0022844
Dec. 7, 2000 (GB) .............................................. 0029920

(51) Int. Cl.[7] ........................ A61K 38/26; C07K 14/605
(52) U.S. Cl. .............................. 514/2; 514/12; 514/102; 514/108; 530/308; 530/324
(58) Field of Search .............................. 514/2, 12, 102, 514/108; 530/308, 324, 303, 300

(56) References Cited

U.S. PATENT DOCUMENTS

| | | |
|---|---|---|
| 5,789,379 A | 8/1998 | Drucker et al. |
| 5,834,428 A | 11/1998 | Drucker |
| 5,912,229 A | 6/1999 | Thim et al. |
| 5,952,301 A | 9/1999 | Drucker |
| 5,990,077 A | 11/1999 | Drucker |
| 5,994,500 A | 11/1999 | Drucker et al. |
| 6,011,155 A * | 1/2000 | Villhauer ................. 544/333 |
| 6,037,143 A | 3/2000 | Wagner et al. |
| 6,048,524 A | 4/2000 | Selden et al. |
| 6,051,557 A | 4/2000 | Drucker |
| 6,077,949 A | 6/2000 | Munroe et al. |
| 6,110,949 A * | 8/2000 | Villhauer ................. 514/365 |
| 6,166,063 A | 12/2000 | Villhauer |
| 6,184,201 B1 | 2/2001 | Drucker et al. |
| 6,416,737 B1 * | 7/2002 | Mangolagas et al. ........ 424/9.2 |

FOREIGN PATENT DOCUMENTS

| | | |
|---|---|---|
| WO | WO 96/32414 | 10/1996 |
| WO | WO 97/31943 | 9/1997 |
| WO | WO 97/39031 | 10/1997 |

(List continued on next page.)

OTHER PUBLICATIONS

Andreasen et al., 1994, "Secretion of glucagon–like peptide–1 and reactive hypoglycemia after partial gastrectomy", Digestion 55:221–228.

(List continued on next page.)

Primary Examiner—Brenda Brumback
Assistant Examiner—Anish Gupta
(74) Attorney, Agent, or Firm—Robert L. Buchanan; Edwards & Angell, LLP

(57) ABSTRACT

The present invention relates to methods for prevention and treatment of bone-related or nutrition-related disorders using a GLP molecule or GLP activator either alone or in combination with another therapeutic. The present invention also encompasses methods of diagnosing or monitoring the progression of a disorder. The invention also encompasses methods of monitoring the effectiveness of treatment of the invention.

3 Claims, 3 Drawing Sheets

FOREIGN PATENT DOCUMENTS

| | | |
|---|---|---|
| WO | WO 98/01535 | 1/1998 |
| WO | WO 98/03547 | 1/1998 |
| WO | WO 98/08872 | 3/1998 |
| WO | WO 98/24813 | 6/1998 |
| WO | WO 98/25644 | 6/1998 |
| WO | WO 98/25955 | 6/1998 |
| WO | WO 98/52600 | 11/1998 |
| WO | WO 99/06059 | 2/1999 |
| WO | WO 99/14239 | 3/1999 |
| WO | WO 99/37793 | 7/1999 |
| WO | WO 99/38501 | 8/1999 |
| WO | WO 99/43361 | 9/1999 |
| WO | WO 99/46283 | 9/1999 |
| WO | WO 99/58144 | 11/1999 |
| WO | WO 00/10549 | 3/2000 |
| WO | WO 00/18371 | 4/2000 |
| WO | WO 00/20592 | 4/2000 |
| WO | WO 00/34331 | 6/2000 |
| WO | WO 00/34332 | 6/2000 |
| WO | WO 00/37053 | 6/2000 |
| WO | WO 00/42026 | 7/2000 |
| WO | WO 00/53208 | 9/2000 |
| WO | WO 01/04156 | 1/2001 |
| WO | WO 01/416779 A2 | 6/2001 |
| WO | WO 02/066062 A2 | 8/2002 |

OTHER PUBLICATIONS

Bell et al., 1983, "Exon duplication and divergence in the human preproglucagon gene", Nature 304:368–371.

Buhl et al., 1988, "Naturally occurring products of proglucagon 111–160 in the porcine and human small intestine.", J. Biol. Chem. 263:8621–8624.

Cheeseman and Tseng, 1996, "The effect of GIP and glucagon–like peptides on intestinal basolateral membrane hexose transport", Am. J. Physiol. 271:G477–G482.

Drucker et al., 1996, "Induction of intestinal epithelial proliferation by glucagon–like peptide 2", Proc. Natl. Acad. Sci. USA 93:7911–7916.

Graham and Malaty, 1999, "Alendronate gastric ulcers", Aliment Pharmacol. Ther. 13:515–519.

Hartmann et al., 2000, "In vivo and in vitro degradation of glucagon–like peptide–2 in humans", J. Clin. Endocrinol. Metab. 85:2884–2888.

Irwin and Wong, 1995, "Trout and chicken proglucagon: alternative splicing generates mRNA transcripts encoding glucagon–like peptide 2", Mol. Endocrinol. 9:267–277.

Jelinek et al., 1993, "Expression cloning and signaling properties of the rat glucagon receptor", Science 259:1614–1616.

Jeppesen et al., 2000, "Elevated plasma glucagon–like peptide 1 and 2 concentrations in ileum resected short bowel patients with a preserved colon", Gut 47:370–376.

Mojsov, 1992, "Structural requirements for biological activity of glucagon–like peptide–I", Intl. J. Pep. Prot. Res. 40:333–343.

Munroe et al., 1999, "Prototypic G protein–coupled receptor for the intestinotrophic factor glucagon–like peptide 2", Proc. Natl. Acad. Sci. USA 96:1569–1573.

Nishi and Steiner, 1990, "Cloning of complementary DNAs encoding islet amyloid polypeptide, insulin, and glucagon precursors from a New World rodent, the degu, *Octodon degu*", Mol. Endocrinol. 4:1192–1198.

Persson et al., 1997, "Hormone replacement therapy and the risk of breast cancer. Nested case–control study in a cohort of Swedish women attending mammography screening", Intl. J. Can. 72:758–761.

Rosenquist et al., 1998, "Serum Crosslaps One Step ELISA. First application of monoclonal antibodies for measurement in serum of bone–related degradation products from C–terminal telopeptides of type I collagen", Clin. Chem. 44:2281–2289.

Schlemmer and Hassager, 1999, "Acute fasting diminishes the circadian rhythm of biochemical markers of bone resorption", Eur. J. Endocrinol.140:332–337.

Schlemmer et al., 1994, "Posture, age, menopause and osteopenia do not influence the circadian variation in the urinary excretion of pyridinium crosslinks", J. Bone Mineral Res. 9:1883–1888.

Thorens, 1992, "Expression cloning of the pancreatic β cell receptor for the gluco–incretin hormone glucagon–like peptide 1", Proc. Natl. Acad. Sci. USA 89:8641–8645.

Unger and Orci, eds., 1981, "Glucagon. Physiology, Pathophysiology, and Morphology of the Pancreatic A–Cells", New York, Elsevier, pp. 104–120.

Francis, "Bisphosphonates in the Treatment of Osteoporosis in 1997: A Review"; Current Therapeutic Research, vol. 58, No. 10, pp. 656–678, 1997.

* cited by examiner

USE OF GLP FOR THE TREATMENT, PREVENTION, DIAGNOSIS, AND PROGNOSIS OF BONE-RELATED AND NUTRITION-RELATED DISORDERS

This application claims priority to co-pending United Kingdom Patent Application No. GB 0022844.5, filed Sep. 18, 2000 and co-pending United Kingdom Patent Application No. GB 0029920.6, filed Dec. 7, 2000, the entire contents of each are incorporated herein by reference in their entirety.

FIELD OF THE INVENTION

The present invention relates to methods for prevention and treatment of bone-related or nutrition-related disorders using a GLP molecule or GLP activator either alone or in combination with another therapeutic. The present invention also encompasses methods of diagnosing or monitoring the progression of a disorder. The invention also encompasses methods of monitoring the effectiveness of treatment of the invention.

BACKGROUND OF THE INVENTION

Glucagon and Related Peptides

Glucagon is a hormone that is released in response to low glucose levels and stimulates glucose production. Thus, it plays a role in counteracting insulin in blood glucose homeostasis (Unger and Orci, 1990, Glucagon in Diabetes Mellitus, $4^{th}$ edition, Elsevier p. 104–120). Glucagon arises from the post-translational processing of a larger precursor molecule, proglucagon.

Proglucagon is produced in both the α-cells of the pancreas as well as in the enteroendocrine L-cells of the intestine. It is subject to differential processing in the different tissues in which it is expressed. For example, glucagon is selectively excised from the precursor in the pancreas while two smaller peptides, glucagon-like peptide-1 (GLP-1) and glucagon-like peptide-2 (GLP-2), are produced in the intestine. GLP-1 and GLP-2 consist of amino acid residues 78–107 and 126–158 of proglucagon respectively (Bell et al., 1983, Nature 304: 368–371; Buhl et al., 1988, J. Biol. Chem., 263:8621; Nishi and Steiner, 1990, Mol. Endocrinol. 4:1192–1198; Irwin and Wong, 1995, Mol. Endocrinol. 9:267–277).

Glucagon and GLP-1 have competing biological activities. GLP-1 stimulates insulin secretion, glucose uptake, and cAMP formation in response to the presence and absorption of nutrients in the gut, whereas glucagon increases glucose output by the liver, skeletal muscle tissue, and adipose tissue during periods of fasting (see, e.g., Mojsov, 1992, Int. J. Pep. Prot. Res. 40:333–343; Andreasen et al., 1994, Digestion 55:221–228). Specific GLP-1 receptors have been identified (Thorens, 1992, Proc. Natl. Acad. Sci. 89:8641–8645) which are distinct from the glucagon receptor (Jelinek et al., 1993, Science 259:1614–1616).

GLP-2 is 33 amino acid fragment of proglucagon. Various vertebrate forms (including human) of GLP-2 have been reported. GLP-2 has intestinotrophic activity (U.S. Pat. No. 5,834,428).

When administered exogenously, GLP-2 can produce a marked increase in the proliferation of small intestinal epithelium in mice, with no apparent side effects (Drucker et al., 1996, Proc. Natl. Acad. Sci. 93:7911–7916). Moreover, GLP-2 increases maximal transport rate of D-glucose across the intestinal basolateral membrane (Cheeseman and Tseng, 1996, Am. J. Phys. 271:G477–G482). GLP-2 may act via a G-protein-coupled receptor (Munroe et al., 1999, Proc. Natl. Acad. Sci. 96:1569–1573).

Disorders

Obesity is one of the most common medical disorders, affecting about 40% of the American population. Mortality from obesity in the United States is estimated at 300,000 to 400,000 per year. Although the etiology of obesity is not fully understood, obesity occurs when energy intake exceeds energy expenditure. Hypothalamic structures, which have complex interconnections with the limbic system and other brain structures, control appetite. In addition, the amount and distribution of a person's body fat may be genetically predetermined and influenced by hormones. Among the agents known to be involved in appetite control are leptin, GLP-1, GLP-2, and neuropeptide-Y.

Osteoporosis is the most common form of metabolic bone disease. It affects more than 25 million people in the United States and causes more than 1.3 million bone fractures each year, including approximately 500,000 spine, 250,000 hip and 240,000 wrist fractures. Hip fractures are the most serious consequence of osteoporosis, with 5–20% of patients dying within one year of the fiacture and over 50% of survivors being incapacitated.

Osteoporosis is commonly observed in post-menopausal women, but it also occurs in elderly and young individuals. The disease is characterized by low bone mass and a deterioration of bone tissue, with a consequent increase in bone fragility and susceptibility to fracture. Although the etiology of osteoporosis is not known, its onset is associated with several factors such as increased age, decreased hormone level, and decreased calcium levels. Osteoporosis may occur in elderly men as androgen levels fall. Androgens play an important role in bone formation/maintenance and promote the synthesis of collagen, which provides a repository for the calcium and phosphorus. Osteoporosis may also be due to increased secretion of parathyroid hormone, which reduces bone formation and enhances bone absorption. Osteoporosis can also be caused by kidney degeneration, which reduces the activity of hydroxylase-activating vitamin D, decreasing intestinal calcium absorption, and precipitating the loss of bone matrix. Mobilization of nutrient stores in bone can be achieved by stimulating osteoclastic bone resorption. Likewise, resorptive activity can be reversed by increasing dietary availability of nutrients.

Dietary intake of calcium has been shown to regulate bone metabolism. Intake of oral glucose has recently been shown to decrease bone resorption, resulting in a fully expressed decrease within two hours following glucose administration (GB Patent Application No. 0007492.2). This response to glucose intake is independent of gender and age. A comparable effect was also demonstrated following protein administration (unpublished communication).

Bone-related disorders are characterized by bone loss resulting from an imbalance between bone resorption and bone formation. The potential for bone loss is directly related to the bone's normal rate of resorption and can amount to over 5% per year in humans immediately following menopause.

There are currently two main types of pharmaceutical treatment for osteoporosis, both aimed at reduction of bone resorption. The first involves the administration of an anti-resorptive compound. For example, estrogen has been used as an anti-resorptive agent to reduce fractures. However, estrogen fails to restore bone to levels of that in a skeleton of a young adult. Furthermore, long-term estrogen therapy has been implicated in a variety of disorders, including an increase in the risk of uterine cancer, endometrial cancer, and possibly breast cancer (Persson et al., 1997, "Hormone replacement therapy and the risk of breast cancer. Nested case-control study in a cohort of Swedish women attending mammography screening", Int. J. Can. 72:758–761). For these reasons, many women avoid treatment of osteoporosis with estrogen.

A second type of pharmaceutical therapy for treating osteoporosis uses an agent that inhibits bone resorption as well as promotes bone formation and increases bone mass. These agents, such as alendronate, typically restore the amount of bone to that of an established premenopausal skeleton. However, alendronate administration can cause undesirable side effects, for example, or gastric ulceration (Graham et al., 1999, Aliment Pharmacol. Ther. 4:515–9).

The significant risks associated with the currently available pharmaceutical therapies (such as estrogen and alendronate) highlight the need to develop safer therapies for treating or preventing osteoporosis and other bone-related disorders. Therefore, there is a need for methods for treating or preventing a bone disorder, such as osteoporosis, that do not carry the aforementioned risks.

SUMMARY OF THE INVENTION

The present invention relates to the prevention or treatment of a bone-related or nutrition-related disorder comprising administering to a patient a composition that increases GLP-2 activity. Compositions of the invention comprise a GLP-2 molecule or a GLP-2 activator. One or more additional therapeutic agents can be administered in conjunction with the compositions of the invention.

Also contemplated by the invention are methods for diagnosing a bone-related or nutrition-related disorders in a patient comprising:
(a) determining the level of GLP-2 molecule expressed in a normal tissue and a test tissue;
(b) comparing said levels of GLP-2 molecule expression in said tissues, wherein a decrease said level of GLP-2 molecule expression in said test tissue indicates a bone-related or nutrition-related disorder.

Also contemplated by the invention are methods of monitoring the progression of a bone-related or nutrition-related disorder in a patient comprising:
(a) determining the level of GLP-2 molecule expressed in a first diseased tissue;
(b) determining the level of GLP-2 molecule expressed in a second diseased tissue, wherein said second diseased tissue is taken from the same patient as said first diseased tissue but at a later date; and
(c) comparing said levels of GLP-2 molecule expression in said first and second diseased tissues, wherein a decrease said level of GLP-2 molecule expression in said second diseased tissue indicates progression of said bone-related or nutrition-related disorder.

Also contemplated by the invention are methods of determining the effectiveness of treatment with a GLP molecule or GLP activator in a patient comprising:
(a) determining the level of one or more markers of bone resorption from a first patient tissue samples prior to said treatment and a second patient tissue sample after said treatment;
(b) comparing said levels of one or more markers in said tissue samples, wherein a decrease in said level in said second tissue sample indicates effective treatment.

Also contemplated by the invention are methods of determining the effectiveness of treatment with a GLP molecule or GLP activator in a patient comprising:
(a) determining the level of one or more markers of nutrition-related disorder from a first patient tissue samples prior to said treatment and a second patient tissue sample after said treatment;
(b) comparing said levels of one or more markers in said tissue samples, wherein a modification in said level in said second tissue sample indicates effective treatment Definitions As used herein, the phrase "GLP" refers to GLP-1 or GLP-2.

As used herein, the phrase "GLP molecules" refers to GLP peptides, fragments of GLP peptides, nucleic acids that encode GLP peptides or fragments, or variants thereof.

As used herein, the term "variant" or "variants" refers to variations of the nucleic acid or amino acid sequence of GLP molecules. Homologues and analogs of a GLP molecule of the invention are contemplated. Encompassed within the term "variant(s)" are nucleotide and amino acid substitutions, additions, or deletions of GLP-1 or GLP-2 molecules. Also encompassed within the term "variant(s)" are chemically modified natural and synthetic GLP-1 or GLP-2 molecules.

As used herein, the term "analog" or "analogs" as used herein refers to a polypeptide that possesses a similar or identical function to a GLP polypeptide or a fragment of a GLP polypeptide, but does not necessarily comprise a similar or identical amino acid sequence of a GLP polypeptide or a fragment of a GLP polypeptide, or possess a similar or identical structure of a GLP polypeptide or a fragment of a GLP polypeptide. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a GLP polypeptide or a fragment of a GLP polypeptide described herein; (b) a polypeptide encoded by a nucleotide sequence that hybridizes under stringent conditions to a nucleotide sequence encoding a GLP polypeptide or a fragment of a GLP polypeptide described herein of at least 10 amino acid residues, at least 15 amino acid residues, at least 20 amino acid residues, at least 25 amino acid residues, or at least 30 amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a GLP polypeptide or a fragment of a GLP polypeptide described herein. A polypeptide with similar structure to a GLP polypeptide or a fragment of a GLP polypeptide described herein refers to a polypeptide that has a similar secondary, tertiary or quaternary structure of a GLP polypeptide or a fragment of a GLP polypeptide described herein. The structure of a polypeptide can determined using methods known to those skilled in the art, including but not limited to, X-ray crystallography, nuclear magnetic resonance, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nuclcotide as the corresponding position in the second sequence, then the molecules are identical at that position. The percent identity between the two sequences is a function of the number of identical positions shared by the sequences (i.e., % identity=number of identical overlapping positions/ total number of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264–2268, modified as in Karlin and Altschul, 1993, Proc. Natl. Acad. Sci. U.S.A. 90:5873–5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389–3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (e.g., http://www.ncbi.nlm.nih.gov). Another preferred, non-limiting example of a mathematical algorithm utilized for the comparison of sequences is the algorithm of Myers and Miller, 1988, CABIOS 4:11–17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "fragment" or "fragments" as used herein refers to a peptide or polypeptide having an amino acid sequence of at least 10 contiguous amino acid residues, at least 15 contiguous amino acid residues, at least 20 contiguous amino acid residues, at least 25 contiguous amino acid residues, or at least 30 contiguous amino acid residues of the amino acid sequence of a GLP polypeptide.

As used herein, the phrase "GLP activator" or "GLP activators" refers to any molecule or compound that increases the activity of GLP in a patient. The invention encompasses, e.g., GLP agonists, GLP receptor agonists, agonist of the GLP signal transduction cascade, compounds that stimulate the synthesis or expression of endogenous GLP, compounds that stimulate release of endogenous GLP, and compounds that inhibit inhibitors of GLP activity (ie., an inhibitor of a GLP antagonist).

As used herein, the term "patient" is an animal, such as, but not limited to, a cow, monkey, horse, sheep, pig, chicken, turkey, quail, cat, dog, mouse, rat, rabbit, and guinea pig, and is more preferably a mammal, and most preferably a human.

As used herein, the phrase "therapy" or "therapeutic agent" refers to any molecule, compound, or treatment that assists in the treatment of a disease, especially a bone-related disorder and a nutrition-related disorder. As such, therapy includes, but is not limited to, radiation therapy, chemotherapy, dietary therapy, physical therapy, and psychological therapy.

As used herein, the phrase "bone-related disorder" refers to a disorder wherein bone formation, deposition, or resorption is abnormal. Bone-related disorders include, but are not limited to, osteoporosis, hypercalcemia of malignancy, osteopenia due to bone metastases, periodontal disease, hyperparathyroidism, periarticular erosions in rheumatoid arthritis, Paget's disease, osteodystrophy, myositis ossificans, Bechterew's disease, malignant hypercalcernia, osteolytic lesions produced by bone metastasis, bone loss due to immobilization, bone loss due to sex steroid hormone deficiency, bone abnormalities due to steroid hormone treatment, bone abnormalities caused by cancer therapeutics, osteomalacia, Bechet's disease, osteomalacia, hyperostosis, osteopetrosis, metastatic bone disease, immobilization-induced osteopenia, and glucocorticoid-induced osteoporosis.

As used herein, the phrase "nutrition-related disorder" refers to a disorder characterized by an abnormal level of food intake or body weight gain/loss and complications from such disorders. Nutrition-related disorders include, but are not limited to, obesity, anorexia, cachexia, bulimia, and other wasting diseases characterized by loss of appetite, diminished food intake, or body weight loss. Complications include, but are not limited to, insulin resistance, diabetes mellitus, hypertension, cardiovascular disease, pseudotumor, cerebri, hyperlipidemia, sleep apnea, cancer, pulmonary hypertension, cardiovascular disease, cholecystitis, and osteoarthritis.

As used herein, the phrase "pharmaceutically acceptable" refers to an agent that does not interfere with the effectiveness of the biological activity of an active ingredient, and which may be approved by a regulatory agency of the Federal government or a state government, or is listed in the U.S. Pharmacopeia or other generally recognized pharmacopeia for use in animals, and more particularly for use in humans. Accordingly, suitable pharmaceutically acceptable carriers include agents that do not interfere with the effectiveness of a pharmaceutical composition.

As used herein, the phrase "pharmaceutically acceptable salts" refers to salts prepared from pharmaceutically acceptable, preferably nontoxic, acids and bases, including inorganic and organic acids and bases, including but not limited to, sulfuric, citric, maleic, acetic, oxalic, hydrochloride, hydro bromide, hydro iodide, nitrate, sulfate, bisulfite, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Pharmaceutically acceptable salts include those formed with free amino groups such as, but not limited to, those derived from hydrochloric, phosphoric, acetic, oxalic, and tartaric acids. Pharmaceutically acceptable salts also include those formed with free carboxyl groups such as, but not limited to, those derived from sodium, potassium, ammonium, sodium lithium, calcium, ferric hydroxides, isopropylamine, triethylamine, 2-ethylamino ethanol, histidine, and procaine.

As used herein, the term "carrier" refers to a diluent, adjuvant, excipient, or vehicle. Such carriers can be sterile liquids, such as saline solutions in water, or oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions.

As used herein, the tern "mineral" refers to a substance, preferably a natural substance, that contain calcium, magnesium or phosphorus. Illustrative nutrients and minerals include beef bone, fish bone, calcium phosphate, egg shells, sea shells, oyster shells, calcium carbonate, calcium chloride, calcium lactate, calcium gluconate and calcium citrate.

As used herein, the term "biological sample" is broadly defined to include any cell, tissue, organ or multicellular organism. A biological sample can be derived, for example, from cells or tissue cultures in vitro. Alternatively, a biological sample can be derived from a living organism or from a population of single cell organisms. Preferably, the biological sample is live tissue. More preferably, the biological sample is live bone or adipose tissue.

As used herein, the term "GIP" refers to glucose-dependent insulinotropic polypeptide. GIP is an incretin that stimulates insulin secretion directly in a glucose-dependent manner.

As used herein, the term "S-CTX" refers to a serum C-telopeptide fragment of collagen type I degradation.

As used herein, the phrase "isolated polypeptide or peptide" refers to a polypeptide or peptide that is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein, peptide, or fragment thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest. In preferred embodiments, purified or isolated preparations will lack any contaminating proteins from the same animal from which the protein is normally produced, as can be accomplished by recombinant expression of, for example, a human protein in a non-human cell.

As used herein, the phrase "isolated nucleic acid molecule" refers to a nucleic acid molecule which is separated from other nucleic acid molecules which are present in the natural source of the nucleic acid molecule. Preferably, an isolated nucleic acid molecule is free of sequences (preferably protein encoding sequences) which naturally flank the nucleic acid (ie., sequences located at the 5' and 3' ends of the nucleic acid) in the genomic DNA of the organism from which the nucleic acid is derived. In other embodiments, the isolated nucleic acid is free of intron sequences. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an isolated nucleic acid molecule, such as a cDNA molecule, can be substantially free of other cellular material, or culture medium when produced by recombinant techniques, or substantially free of chemical precursors or other chemicals when chemically synthesized. In one embodiment, the nucleic acid molecules of the invention comprise a contiguous open reading frame encoding a polypeptide of the invention.

As used herein, the phrase "hybridizes under stringent conditions" is intended to describe conditions for hybridization and washing under which nucleotide sequences at least 60% (65%, 70%, 75%, 80%, or preferably 85% or more) identical to each other typically remain hybridized to each other. Such stringent conditions are known to those skilled in the art and can be found in *Current Protocols in Molecular Biology*, John Wiley & Sons, N.Y. (1989), 6.3.1–6.3.6, which describes aqueous and non-aqueous methods, either of which can be used. Another preferred, non-limiting example of stringent hybridization conditions are hybridization in 6×sodium chloride/sodium citrate (SSC) at about 45° C., followed by one or more washes in 2.0×SSC at 50° C. (low stringency) or 0.2×SSC, 0.1% SDS at 50–65° C. (high stringency). Another preferred example of stringent hybridization conditions are hybridization in 6×sodium chloride/sodium citrate (SSC) at about 45° C., followed by one or more washes in 0.2×SSC, 0.1% SDS at 50° C. Another example of stringent hybridization conditions are hybridization in 6×sodium chloride/sodium citrate (SSC) at about 45° C., followed by one or more washes in 0.2×SSC, 0.1% SDS at 55° C. A further example of stringent hybridization conditions are hybridization in 6×sodium chloride/sodium citrate (SSC) at about 45° C., followed by one or more washes in 0.2×SSC, 0. 1% SDS at 60° C. Preferably, stringent hybridization conditions are hybridization in 6×sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5 M Sodium Phosphate, 7% SDS at 65° C., followed by one or more washes at 0.2×SSC, 1% SDS at 65° C. In one embodiment, an isolated nucleic acid molecule of the invention that hybridizes under stringent conditions to the sequence of the GLP nucleic acid, or a complement thereof, corresponds to a naturally-occurring nucleic acid molecule. As used herein, a "naturally occurring" nucleic acid molecule refers to an RNA or DNA molecule having a nucleotide sequence that occurs in nature (e.g. encoding a natural protein).

DETAILED DESCRIPTION OF THE INVENTION

Figure 1A:
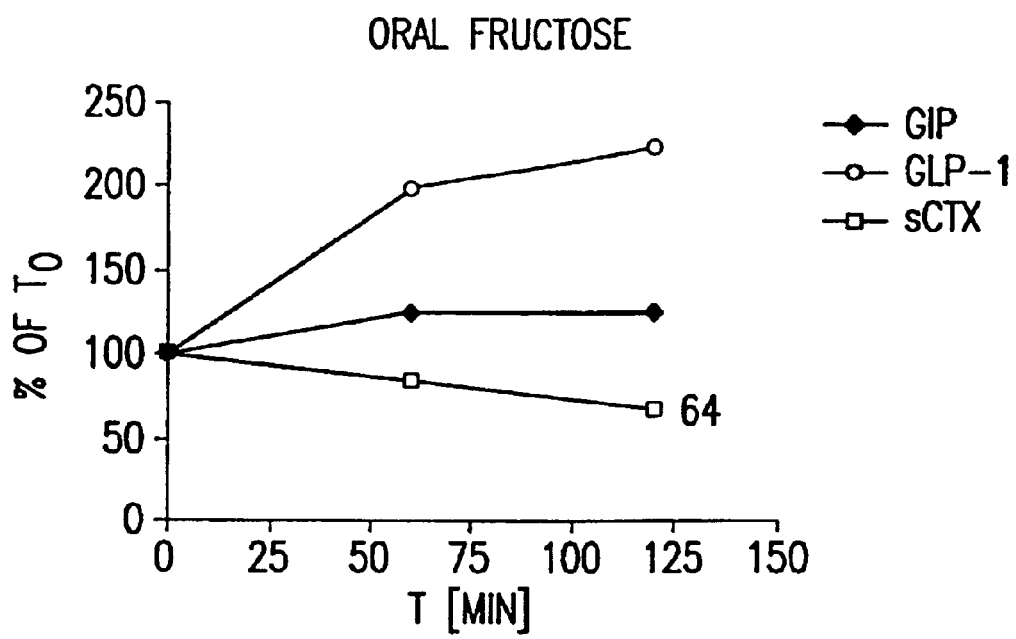
FIG. 1 shows the levels of GLP-1, GIP and S-CTX over a 2–3 hour period in response to (A) oral fructose; (B) oral long chain fatty acid; (C) oral protein.

GLP and Bone-related Disorders or Nutrition-related Disorders

The present invention is based, in part, on Applicant's discovery that GLP-1 and GLP-2 inhibit bbne resorption and promote bone formation. Without being bound by any theory, Applicant believes that, as observed for parathyroid hormone (PTH) and prostaglandin E2 (PGE2), GLP-1 and GLP-2 exert an anabolic bone effect, particularly by increasing cAMP. The anti-resorptive effects of GLP might result from its ability to inhibit IL-6 secretion, oppose PTH action, and/or create a hypogonadal state that contributes to the anti-resorptive effects of GLP.

Therefore, GLP molecules and GLP activators disclosed herein are useful for treating or preventing a bone-related disorder, including a bone-related disorder disclosed herein.

The GLP molecules and GLP activators disclosed herein are also useful for treating or preventing a nutrition-related disorder and those complications resulting from said nutrition-related disorder. GLP molecules effect blood glucose levels and maintain or restore gastrointestinal function.

A GLP molecule or GLP activator can also activate one or more receptors present in bone-derived cells. Without being bound by any theory, stimulation of these cells with GLP can lead to an increase in intracellular calcium concentration, an increase in cellular cAMP content, a stimulation of type I collagen synthesis, and inhibition of PTH-stimulated bone resorption.

In accordance with the invention, the present compositions and methods can be used to intercede upstream or downstream in the signal transduction cascade involved in GLP action to reduce the rate of bone resorption and/or to promote the rate of bone formation. In one embodiment, the synthesis or release of endogenous GLP can be stimulated. In another embodiment, the endogenous synthesis or release of another molecule active in the cascade downstream from GLP, (e.g., a molecule produced in response to GLP binding to a receptor), can be stimulated.

Accordingly, the methods and compositions of the invention are useful for preventing, treating, diagnosing, or monitoring the progression a bone-related disorder, including a bone-related disorder disclosed herein.

GLP Molecules

The GLP molecules can be used in the present methods and compositions for treating or preventing a bone-related disorder, or a nutrition-related disorder.

In one embodiment, the GLP molecule is a GLP nucleic acid encoding a GLP polypeptide, peptidc, or fragment thereof. The GLP nucleic acid is, for example, a full-length cDNA, cDNA corresponding to a protein coding region, RNA, mRNA, oligonucleotide, consensus sequence, motif, restriction fragment, antisense molecule, ribozyme, or a molecule encoding a protein domain.

In another embodiment, the GLP molecule is a GLP polypeptide or peptide, or fragment thereof. The GLP polypeptide or peptide is, for example, a full-length protein, receptor binding domain, catalytic domain, signal sequence, or protein motif.

Moreover, any GLP molecule that contains additional nucleic acid or amino acid residues, or has nucleic acids or amino acids deleted from it can be used in the present methods and compositions of the invention. Additionally, GLP molecules of the invention may contain substituted nucleic acids or amino acids. In one embodiment, the GLP variant has enhanced activity compared to native human GLP-2. For example, such GLP variants can exhibit enhanced serum stability, enhanced receptor binding, or enhanced signal transducing activity. Amino acid modifications, substitutions, additions, or truncations that render a GLP peptide resistant to oxidation or degradation are contemplated by the present invention. In a preferred embodiment, the GLP variants are derived from human or rat GLP sequences.

Molecules contemplated as GLP peptides, in accordance with the present invention are known in the art (See, e.g., U.S. Pat. No. 5,990,077; International Patent Application Nos. WO 00/34331 and WO 00/34332). For example, International Patent Application Nos. WO 00/34331 and WO 00/34332 disclose analogues of GLP-1 such as (Aib$^{8,35}$) hGLP-1(7-36)NH$_2$, and (Aib$^8$,β-Ala$^{35}$)hGLP-1(7-36)NH$_2$. And U.S. Pat. No. 5,990,077, discloses forms of GLP-2 and the pharmaceutically acceptable acid salts thereof, that conform to the general formula:

R1-[Y]m-His-Ala-Asp-Gly-Ser-Phe-Ser-Asp-Glu-Met-Asn-Thr-aa1-Leu-Ala-aa2-Leu-Ala-aa3-Arg-Asp-Phe-Ile-Asn-Trp-Leu-aa4-aa5-Thr-Lys-Ile-Thr-Asp-[X]-n-R2.

Many variants of GLP-1 are known in the art such as, for example, Gln9-GLP-1, D-Gln9-GLP-1, acetyl-Lys9-GLP-1, Thr16-Lys18-GLP-1, and Lys18-GLP-1 as listed in WO 91/11457. Acid addition salts, carboxylate salts, lower alkyl esters, and amides of GLP-1 variants, many of which are disclosed in the art, are also contemplated by the invention.

Variants of GLP-1 can be obtained by fragmenting a naturally occurring sequence, or can be synthesized based upon knowledge of the DNA, RNA, or amino acid sequence of a native GLP-1. Processes for preparing these variants are known to those of ordinary skill in the art (See, e.g., WO 91/11457; U.S. Pat. Nos. 5,118,666, 5,120,712, and 5,512, 549). For example, variants can be prepared using standard solid-phase techniques for the synthesis of peptides. As is generally known, peptides of the requisite length can be prepared using commercially available equipment and reagents following the manufacturers' instructions for blocking interfering groups, protecting the amino acid to be reacted, coupling, deprotection, and capping of unreacted residues. Suitable equipment can be obtained, for example, from Applied BioSystems in Foster City, Calif., or Biosearch Corporation in San Raphael, Calif. It is also possible to obtain fragments of GLP-1, by fragmenting the naturally occurring amino acid sequence, using, for example, a proteolytic enzyme. Further, it is possible to obtain the desired fragments of the GLP-1 through the use of recombinant DNA technology. The basic steps in recombinant production are:

a) isolating a natural DNA sequence encoding GLP-1 or constructing a synthetic or semi-synthetic DNA coding sequence for GLP-1, b) placing the coding sequence into an expression vector in a manner suitable for expressing proteins either alone or as a fusion proteins, c) transforming an appropriate eukaryotic or prokaryotic host cell with the expression vector, d) culturing the transformed host cell under conditions that will permit expression of a GLP-1 intermediate, and e) recovering and purifying the recombinantly produced protein.

In one embodiment, the GLP molecule is a GLP-1 variant having enhanced insulin-stimulating properties as disclosed in U.S. Pat. No. 5,545,618. The variants can be GLP-1(7-34); (7-35); (7-36) or (7-37) human peptide or the C-terminal amidated forms thereof. The native peptides have the amino acid sequence (wherein the first amino acid below (i.e., His) is at position 7):
His-Ala-Gln-Gly-Thr-Phe-Thr-Ser-Asp-Val-Ser-Ser-Tyr-Leu-Gin-Gly-Glu-Ala-Ala-Lys-Gln-Phe-Ile-Ala-Trp-Leu-Val-Lys-(Gly)-(Arg)-(Gly) wherein (Gly), (Arg), and (Gly) are present or absent depending on indicated chain length.

The variants have the foregoing sequence, or the C-terminal amide thereof, with at least one modification selected from the group consisting of:

(a) substitution of a neutral amino acid, arginine, or a D form of lysine for lysine at position 26 and/or 34 and/or a neutral amino acid, lysine, or a D form of arginine for arginine at position 36;

b) substitution of an oxidation-resistant amino acid for tryptophan at position 31;

(c) substitution according to at least one of:
Tyr for Val at position 16;
Lys for Ser at position 18;
Asp for Gln at position 21;
Ser for Gly at position 22;
Arg for Glu at position 23;
Arg for Ala at position 24; and
Glu for Lys at position 26;

(d) a substitution comprising at least one of:
an alternative small neutral amino acid for A at position 8;
an alternative acidic amino acid or neutral amino acid for Glu at position 9;
an alternative neutral amino acid for Gly at position 10; and
an alternative acidic amino acid for Asp at position 15; and (e) substitution of an alternative neutral amino acid or the D or N-acylated or alkylated form of histidine for histidine at position 7.

In another embodiment, the GLP molecule is a GLP-1 variant having enhanced resistance to degradation as compared to native GLP-1. Enhanced resistance to degradation can result in longer bioavailability. In a specific embodiment, the GLP-1 variant demonstrates both enhanced insulin-release stimulating activity and enhanced stability.

In another embodiment, the GLP molecule is a GLP-2 variant. GLP-2 variants are known in the art. Examples of GLP-2 variants are found in U.S. Pat. Nos. 5,990,077 and 6,184,201, and include the following:

1) His-Ala-Asp-Gly-Ser-Phe-Ser-Asp-Glu-Met-Asn-Thr-Ile-Leu-Asp-Asn-Leu-Ala-Thr-Arg-Asp-Phe-Ile-Asn-Trp-Leu-Ile-Gln-Thr-Lys-Ile-Thr-Asp.

2) R1-[Y]m-His-Ala-Asp-Gly-Ser-Phe-Ser-Asp-Glu-Met-Asn-Thr-aa1-Leu-Asp-aa2-Leu-Ala-aa3-Arg-Asp-Phe-Ile-Asn-Trp-Leu-aa4-aa5-Thr-Lys-Ile-Thr-Asp-[X]n-R2.

wherein:
aa1 is a neutral, polar, large and nonaromatic amino acid residue;
aa2 is a neutral and polar amino acid residue;
aa3 is a neutral amino acid residue;
aa4 is a neutral, polar, large and nonaromatic amino acid residue;
aa5 is a neutral or basic amino acid residue;
X is Arg, Lys, Arg-Lys or Lys-Lys;
Y is Arg or Arg-Arg;
m is 0 or 1;
n is 0 or 1;
R1 is H or an N-terminal blocking group; and
R2 is OH or a C-terminal blocking group.

3) R1-[Y]m-His-Ala-Asp-Gly-Ser-Phe-Ser-Asp-Glu-Met-Asn-Thr-aa1-Leu-Asp-aa2-Leu-Ala-aa3-Arg-Asp-Phe-Ile-Asn-Trp-Leu-aa4-aa5-Thr-Lys-Ile-Thr-Asp-[X]n-R2 wherein:
aa1 is Ile or Val;
aa2 is Asn or Ser;
aa3 is Ala or Thr;
aa4 is Ile or Leu;
aa5 is Gln or His;
X is Arg, Lys, Arg-Lys or Lys-Lys;
Y is Arg or Arg-Arg;
m is 0 or 1;
n is 0 or 1;
R1 is H or an N-terminal blocking group; and
R2 is OH or a C-terminal blocking group.

4) R1-(Y1)m-X1-X2-X3-X4-Ser5-Phe6-Ser7-Asp8-(P1)-Leu14-Asp15-Asn16-Leu 17-Ala18-X19-X20-Asp21-Phe22-(P2)-Trp25-Leu26-Ile27-Gln28-Thr29-Lys30-(P3)-(Y2)n-R2, wherein
X1 is His or Tyr
X2 is Ala or an Ala-replacement amino acid conferring on said analog resistance to DPP-IV enzyme;
X3 is Pro, HPro, Asp or Glu;
X4 is Gly or Ala;
P1 is Glu-X10-Asn-Thr-Ile or Tyr-Ser-Lys-Tyr;
X10 is Met or an oxidatively stable Met-replacement amino acid;
X19 is Ala or Thr;
X20 is Arg, Lys, His or Ala;
P2 is Ile-Asn, Ile-Ala or Val-Gln;
P3 is a covalent bond, or is Ile, Ile-Thr or Ile-Thr-Asn;
R1 is H or an N-terminal blocking group;
R2 is OH or a C-terminal blocking group;
Y1 is one or two basic amino acids selected from the group Arg, Lys, and His;
Y2 is one or two basic amino acids selected from the group Arg, Lys, and His; and
m and n, independently, are 0 or 1; and
wherein at least one of X1, X2, X3, X4, P1, X10, X19, X20, P2 and P3 is other than a wild type, mammalian GLP-2 residue.

In one embodiment, the GLP-2 variant is resistant to cleavage by dipeptidyl peptidase-IV (DPP-IV).

In another embodiment, the GLP-2 variant has an amino acid sequence wherein an oxidatively sensitive amino acid, is replaced with an oxidatively stable amino acid residue. In another embodiment, the oxidatively sensitive amino acid is methionine ("Met"). These variants can be more stable than a native GLP-2.

In another embodiment, the GLP-2 variant has an amino acid sequence wherein an arginine is replaced with a basic amino acid (e.g., histidine or lysine).

GLP Activators

The invention also encompasses molecules that serve to increase GLP activity (GLP activators) for use in prevention and treatment of bone-related and nutritional-related disorders. For example, GLP agonists, GLP receptor agonists, agonist of the GLP signal transduction cascade, compounds that stimulate the synthesis or expression of endogenous GLP, compounds that stimulate release of endogenous GLP, and compounds that inhibit inhibitors of GLP activity (i.e., an inhibitor of a GLP antagonist) are contemplated.

In one embodiment, the GLP activator is a GLP-2 agonist. GLP-2 agonists are known in the art and are listed below (See also, e.g., U.S. Pat. No. 6,051,557).

In specific embodiments of the invention, the GLP-2 agonist comprises an amino acid having the sequence:

His-Ala-Asp-Gly-Ser-Phe-Ser-Asp-Glu-Met-Asn-Thr-Ile-Leu-Asp-Asn-Leu-Ala-Thr-Arg-Asp-Phe-Ile-Asn-Trp-Leu-Ile-Gln-Thr-Lys-Ile-Thr-Asp; or

His-Ala-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp; or

His-Gly-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp.

In a particular embodiment, GLP-2 agonists have a(n):

N-terminal blocking group; and/or

N-terminal extension such as Arg or Arg-Arg; and/or

C-terminal blocking group; and/or

C-terminal extension such as Arg or Arg-Arg.

In another embodiment, the GLP molecule useful for the invention is an inhibitor of a GLP antagonist. In a particular embodiment, the GLP antagonist is a protease. In a specific embodiment, the protease is DPP-IV.

Useful inhibitors of the GLP antagonist, DPP-IV, include, but are not limited to, N-(substituted glycyl)-2-cyanopyrrolidines, N-Ala-Pro-O-(nitrobenzyl-) hydroxylamine, and ε-(4-nitro) benzoxycarbonyl-Lys-Pro. Other useful inhibitors of DPP-IV are known in the art (See, e.g., U.S. Pat. Nos. 5,462,928 (columns 2–4), 5,543,396 (column 2) and 6,124,305 (columns 1–2). Some examples are: X-Pro-Y-boroPro, where X and Y are chosen from any amino acid residue, and where boroPro is used to designate an α-amino boronic acid analog of proline which has the carboxyl group of proline replaced with a B(OH)$_2$ group; peptidyl derivatives of aromatic diesters of α-aminoalkylphosphonic acids; and N-substituted glycyl)-2-cyanopyrrolidines.

In yet another embodiment, the inhibitor of a GLP antagonist is an antibody directed against a GLP antagonist. In a further embodiment, the inhibitor is an antibody directed against DPP-IV (See, e.g., U.S. Pat. No. 6,265,551). For example, U.S. Pat. No. 6,265,551 discloses antibodies that bind specifically to the 175 kDa form of DPPIV/CD26 but not to the 105 kDa form.

Also encompassed by the invention are nucleic acid molecules encoding GLP activators that are polypeptides. The nucleic acid is preferably found in a mammalian expression vector comprising a tumor-specific, tissue-specific, and/or inducible transcriptional regulatory sequence.

Screening Assays to Identify GLP Activators

The invention provides a method (also referred to herein as a "screening assay") for identifying GLP activators from candidate or test compounds or agents (e.g., peptides, peptidomimetics, small molecules or other drugs) which have a modulatory (i.e., stimulatory or inhibitory) effect on, for example, expression or activity of a GLP molecule the invention.

The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994,. J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented in solution (e.g., Houghten, 1992, Bio/Techniques 13:412–421), or on beads (Lam, 1991, Nature 354:82–84), chips (Fodor, 1993, Nature 364:555–556), bacteria (U.S. Pat. No. 5,223,409), spores (U.S. Pat. Nos. 5,571,698; 5,403,484; and 5,223, 409), plasmids (Cull et al., 1992, Proc. Natl. Acad. Sci. USA 89:1865–1869) or phage (Scott and Smith, 1990, Science 249:386–390; Devlin, 1990, Science 249:404–406; Cwirla et al., 1990, Proc. Natl. Acad. Sci. USA 87:6378–6382; and Felici, 1991, J. Mol. Biol. 222:301–310).

In one embodiment, an assay is a cell-based assay in which a cell that expresses a GLP molecule, or a biologically active portion thereof, is contacted with a test compound and the ability of the test compound to bind to the GLP molecule is determined. The cell, for example, can be a yeast cell or a cell of mammalian origin. Determining the ability of the test compound to bind to the GLP molecule can be accomplished, for example, by coupling the test compound with a radioisotope or enzymatic label such that binding of the test compound to the GLP molecule or biologically active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a GLP molecule, or a biologically active portion thereof, with a known compound which binds the polypeptide to form an assay mixture, contacting the assay mixture with a test compound, and determining the ability of the test compound to interact with the GLP molecule, wherein determining the ability of the test compound to interact with the GLP molecule comprises determining the ability of the test compound to preferentially bind to the GLP molecule or a biologically active portion thereof as compared to the known compound.

In another embodiment, the assay involves assessment of an activity characteristic of the GLP molecule, wherein binding of the test compound with the GLP molecule or a biologically active portion thereof alters (e.g., increases or decreases) the activity of the GLP molecule.

In another embodiment, an assay is a cell-based assay comprising contacting a cell expressing a GLP molecule, or a biologically active portion thereof, with a test compound and determining the ability of the test compound to modulate (e.g., stimulate or inhibit) the activity of the GLP molecule or biologically active portion thereof. Determining the ability of the test compound to modulate the activity of the GLP molecule or a biologically active portion thereof can be accomplished, for example, by determining the ability of the GLP molecule to bind to or interact with a target molecule.

Determining the ability of a GLP molecule to bind to or interact with a target molecule can be accomplished by one of the methods described above for determining direct binding. As used herein, a "target molecule" is a molecule with which a selected GLP molecule binds or interacts with in nature. For example, a target molecule can be a component of a signal transduction pathway which facilitates transduction of an extracellular signal through the cell membrane and into the cell or a second intercellular protein which has catalytic activity or a protein which facilitates the association of downstream signaling molecules with a GLP molecule. Determining the ability of a GLP molecule to bind to or interact with a target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, e.g. luciferase), or detecting a cellular response, for example, cellular differentiation, or cell proliferation.

In yet another embodiment, an assay of the present invention is a cell-free assay comprising contacting a GLP molecule or biologically active portion thereof with a test compound and determining the ability of the test compound to bind to the GLP molecule or biologically active portion thereof. Binding of the test compound to the GLP molecule can be determined either directly or indirectly as described above. In a preferred embodiment, the assay includes contacting the GLP molecule or biologically active portion thereof with a known compound which binds the GLP molecule to form an assay mixture, contacting the assay mixture with a test compound, and determining the ability of the test compound to interact with the GLP molecule, wherein determining the ability of the test compound to interact with the GLP molecule comprises determining the ability of the test compound to preferentially bind to the GLP molecule or biologically active portion thereof as compared to the known compound.

In another embodiment, an assay is a cell-free assay comprising contacting a GLP molecule or biologically active portion thereof with a test compound and determining the ability of the test compound to modulate (e.g., stimulate or inhibit) the activity of the GLP molecule or biologically active portion thereof. Determining the ability of the test compound to modulate the activity of the GLP molecule can be accomplished, for example, by determining the ability of the polypeptide to bind to a target molecule by one of the methods described above for determining direct binding. In an alternative embodiment, determining the ability of the test compound to modulate the activity of the GLP molecule can be accomplished by determining the ability of the polypeptide of the invention to further modulate the target molecule. For example, the catalytic/enzymatic activity of the target molecule on an appropriate substrate can be determined as previously described.

In yet another embodiment, the cell-free assay comprises contacting a GLP molecule or biologically active portion thereof with a known compound which binds the GLP molecule to form an assay mixture, contacting the assay mixture with a test compound, and determining the ability of the test compound to interact with the GLP molecule, wherein determining the ability of the test compound to interact with the GLP molecule comprises determining the ability of the polypeptide to preferentially bind to or modulate the activity of a target molecule.

In more than one embodiment of the above assay methods of the present invention, it may be desirable to immobilize either the GLP molecule or its target molecule to facilitate separation of complexed from uncomplexed forms of one or both of the molecules, as well as to accommodate automation of the assay. Binding of a test compound to the GLP molecule, or interaction of the GLP molecule with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione sepharose beads or glutathione derivatized microtiter plates, which are then combined with the test compound or the test compound and either the non-adsorbed target molecule or a GLP molecule, and the mixture incubated under conditions conducive to complex formation (e.g., at physiological conditions for salt and pH). Following incubation, the beads or microtiter plate wells are washed to remove any unbound components and complex formation is measured either directly or indirectly, for example, as described above. Alternatively, the complexes can be dissociated from the matrix, and the level of binding or activity of the polypeptide of the invention can be determined using standard techniques.

Other techniques for immobilizing proteins on matrices can also be used in the screening assays of the invention. For example, either the GLP molecule or its target molecule can be immobilized utilizing conjugation of biotin and streptavidin. Biotinylated polypeptide of the invention or target molecules can be prepared from biotin-NHS (N-hydroxysuccinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the GLP molecule or target molecules but which do not interfere with binding of the polypeptide of the invention to its target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention or target molecule.

In another embodiment, modulators of expression of a GLP molecule of the invention are identified in a method in which a cell is contacted with a candidate compound and the expression of the selected mRNA or protein (i.e., the mRNA or protein corresponding to a GLP molecule) in the cell is determined. The level of expression of the selected mRNA or protein in the presence of the candidate compound is compared to the level of expression of the selected mRNA or protein in the absence of the candidate compound. The candidate compound can then be identified as a modulator of expression of the GLP molecule based on this comparison. For example, when expression of the selected mRNA or protein is greater (statistically significantly greater) in the presence of the candidate compound than in its absence, the candidate compound is identified as a stimulator of the selected mRNA or protein expression. Alternatively, when expression of the selected mRNA or protein is less (statistically significantly less) in the presence of the candidate compound than in its absence, the candidate compound is identified as an inhibitor of the selected mRNA or protein expression. The level of the selected mRNA or protein expression in the cells can be determined by methods described herein.

In yet another aspect of the invention, a GLP molecule can be used as "bait proteins" in a two-hybrid assay or three hybrid assay (see, e.g., U.S. Pat. No. 5,283,317; Zervos et al., 1993, *Cell* 72:223–232; Madura et al., 1993, *J. Biol. Chem.* 268:12046–12054; Bartel et al., 1993, *Bio/Techniques* 14:920–924; Iwabuchi et al., 1993, *Oncogene* 8:1693–1696; and PCT Publication No. WO 94/10300), to identify other proteins, which bind to or interact with a GLP molecule and modulate activity of the GLP molecule. Such binding proteins are also likely to be involved in the propagation of signals by the polypeptide of the inventions as, for example, upstream or downstream elements of a signaling pathway involving a GLP molecule.

This invention further pertains to novel agents identified by the above-described screening assays and uses thereof for treatments as described herein.

Methods of using the GLP molecules and GLP activators

The GLP molecules or GLP activators are administered to a patient, preferably a mammal, more preferably a human, for the treatment or prevention of a bone-related disorder or a nutrition-related disorder. The GLP molecules or GLP activators of the invention can be used to treat acute or chronic forms of these conditions.

Also contemplated are methods of prevention or treatment involving combination therapies comprising administering an effective amount of a GLP molecule or GLP activator in combination with another therapeutic agent or agents. The other therapeutic agent or agent can be, for example, an anti-osteoporosis agent, a steroid hormones, a non-steroid hormone, growth factor, a selective estrogen receptor modulator, an insulin-releasing agent, an inhibitor of glucagon secretion, a glucagon antagonists, a circadian rhythm regulator, a growth hormone secretagogue, an agent that increase IGF-1 levels, an immunotherapeutic agent, a cytokine, a protease inhibitor, a vitronectin receptor antagonist, a bisphosphonate compound, a kinase inhibitor, an integrin receptor or antagonist thereof, an anti-obesity agent, a lipid-metabolism improving agent, a neuropeptide Y blocker, a kainate/AMPA receptor antagonist, a β-adrenergic receptor agonist, a compound that reduces caloric intake, an anti-diabetes agent, or a dietary nutrient. Examples of therapeutic agents include, but are not limited to, those in Table 1.

TABLE 1

Other Therapeutics to be Administered with GLP Molecules or Activators anti-osteoporosis agent alendronate sodium
caicium L-threonate (e.g., $C_8H_{14}O_{10}Ca$)
clodronate
etidronate
gallium nitrate
mithramycin TABLE 1-continued Other Therapeutics to be Administered with GLP Molecules or Activators norethindrone acetate (e.g., that which is commercially available as ACTIVELLA)
osteoprotegerin
pamidronate
risedronate sodium
steroid hormones androgen (e.g., androstenedione, testosterone, dehydroepiandrosterone, dihydrotestosterone, 7-alpha-methyl-19-nortestosterone, 7-alpha-methyl-19-nortestosterone acetate, methandroil, oxymetholone, methanedione, oxymesterone, nordrolone phenylpropionate, norethandrolone)
glucocorticoid
estrogenic hormones (e.g., that which is commercially available as PREMARIN)
progestin
non-steroid hormone calcitonin
calcitriol
growth hormone (e.g., osteoclast-activating factor)
melatonin
parathyroid hormone
prostaglandin
thyroid hormone
growth factor epidermal growth factor
fibroblast growth factor
insulin-like growth factor 1
insulin-like growth factor 2
platelet-derived growth factor
vascular endothelial growth factor
selective estrogen receptor modulator BE-25327
CP-336156
clometherone
delmadinone
droloxifene
idoxifene
nafoxidine
nitromifene
ormeloxifene
raloxifene (e.g., that which is commercially available as EVISTA)
tamoxifen
toremifene
trioxifene
[2-4-hydroxyphenyl)-6-hydroxynaphthalen-1-yl][4-[2-1-piperidinyl)-ethoxy]phenyl]-methane
insulin-releasing agent GLP-1
nateglinide
repaglinide (e.g., that which is commercially available as PRANDIN)
sulfonylurea (e.g., glyburide, glipizide, glimepiride)
vasopressin
inhibitor of glucagon secretion somatostatin
glucagon antagonists substituted glucagons having an alanine residue at position 1, 2, 3–5, 9–11, 21, or 29
des-His$^1$-Ala$^2$ glucagons
des-His$^1$-[Ala$^{2,11}$-Glu$^{21}$] glucagon
circadian rhythm regulator alkylene dioxybenzene agonist
melatonin
neuropeptide Y
tachykinin agonist
visible light therapy
growth hormone secretagogue cycloalkano[b]thien-4-ylurea
GHRP-1
GHRP-6

TABLE 1-continued

Other Therapeutics to be Administered with GLP Molecules or Activators growth hormone releasing factor
hexarelin
thiourea
B-HT920
benzo-fused lactams (e.g., N-biphenyl-3-amido substituted benzolactams)
benzo-fused macrocycles (e.g., 2-substituted piperidines, 2-substituted pyrrolidines, 2-substituted hexahydro-1H-azepines, di-substituted piperidines, di-substituted pyrrolidines, di-substituted hexahydro-1H-azepines, tri-substituted piperidines, tri-substituted pyrrolidines, tri-substituted hexahydro-1H-azepines, L-pyroglutamyl-pyridylalanyl-L-prolinamides)
agents that increase IGF-1 levels L-acetylcarnitine
L-isovalerylcarnitine
L-propionylcarnitine
immunotherapeutic agent antibody
immunomodulator
cytokine endothelial monocyte activating protein
granulocyte colony stimulating factor
interferon (e.g., IFN-γ)
interleukin (e.g., IL-6)
lymphokine
lymphotoxin-α
lymphotoxin-β
tumor necrosis factor
tumor necrosis-factor-like cytokine
macrophage inflammatory protein
monocyte colony stimulating factor
4-1BBL
CD27 ligand
CD30 ligand
CD40 ligand
CD137 ligand
Fas ligand
OX40 ligand
protease inhibitor cysteine protease inhibitor (e.g., vinyl sulfone, peptidylfluoromethyl ketone, cystatin C, cystatin D, E-64)
DPP IV antagonist
DPP IV inhibitor (e.g., N-(substituted glycyl)-2-cyanopyrrolidines, N—Ala—Pro—O-nitrobenzyl-hydroxylamine, and ε-(4-nitro)-benzoxycarbonyl-Lys—Pro)
serine-protease inhibitor (e,g., azapeptide, BMS232632, antipain, leupeptin)
vitronectin receptor antagonist anti-vitronectin receptor antibody (e.g., 23C6)
cyclo-S,S-N α-acetyl-cysteinyl-N alpha-methyl-argininyl-glycyl-aspartyl-penicillamine
RGD-containing peptide (e.g., echistatin)
bisphosphonate compound alendronate (e.g., that which is commercially available as FOSAMAX)
aminoalkyl bisphosphonate (e.g., alendronate, pamidronate(3-amino-1-hydroxypropylidene)bisphosphonic acid disodium salt, pamidronic acid, risedronate(1-hydroxy-2-(3-pyridinyl)ethylidene)bisphosphonate, YM 175 [(cycloheptylamino)methylene-bisphosphonic acid], piridronate, aminohexanebisphosphonate, tiludronate, BM-210955, CGP-42446, EB-1053)
risedronate (e.g., that which is commercially available as ACTONEL)
kinase inhibitor Rho-kinase inhibitor (e.g., (+)-trans-4-(1-aminoethyl)-1-(4-pyridyl-carbamoyl)cyclohexane, trans-N-(1H-pyrrolo[2,3-b]pyridin-4-yl)-4-guanidinomethylcyclohexanecarboxamide, 1-(5-isoquinolinesulfonyl)-homopiperazine, 1-(5-isoquinolinesulfonyl)-2-methylpiperazine)
integrin receptor α subunit (e.g., subtype 1–9, D, M, L, X, V, IIb, IELb)
β subunit (e.g., subtype 1–8)

TABLE 1-continued

Other Therapeutics to be Administered with GLP Molecules or Activators integrin receptor antagonists ethyl 3(S)-(2,3-dihydro-benzofuran-6-yl)-3-{2-oxo-3-[3-(5,6,7,8-tetrahydro-[1,8]naphthyridin-2-yl)-propyl]-tetrahydro-pyrimidin-1-yl}-propionate;
ethyl 3(S)-(3-fluorophenyl)-3-(2-oxo-3(S or R)-[3-(5,6,7,8-tetrahydro-[1,8]naphthyridin-2-yl)-propyl]-piperidin-1-yl)-propionate;
ethyl 3(S)-(3-fluorophenyl)-3-(2-oxo-3 ® or S)-[3-(5,6,7,8-tetrahydro-[1,8]naphthyridin-2-yl)-propyl]-piperidin-1-yl)-propionate;
3(S)-(2,3-dihydro-benzofuran-6-yl)-3-{2-oxo-3-[3-(5,6,7,8-tetrahydro-[1,8]naphthyridin-2-yl)-propyl]-tetrahydro-pyrimidin-1-yl}-propionic acid;
3(S)-(3-fluorophenyl)-3-(2-oxo-3(S or R)-[3-(5,6,7,8-tetrahydro-[1,8]-naphthyridin-2-yl)-propyl]-piperidin-1-yl)-propionic acid;
3(S)-(3-fluorophenyl)-3-(2-oxo-3 ® or S)-[3-(5,6,7,8-tetrahydro-[1,8]naphthyridin-2-yl)propyl]-piperidin-1-yl)-propionic acid
anti-obesity agent benzphetamine (e.g. that which is commercially available as DIDREX)
benzylisopropylamine (e.g. that which is commercially available as IONAMIN)
bupropion
dexfenfluramine (e.g. that which is commercially available as REDUX)
dextroamphetamine (e.g. that which is commercially available as DEXEDRINE)
diethylpropion (e.g. that which is commercially available as TENUATE)
dimethylphenethylamine (e.g. that which is commercially available as ADIPEX or DESOXYN)
evodamine
fenfluramine (e.g. that which is commercially available as PONDIMIN)
fluoxetine
mazindol (e.g. that which is commercially available as SANOREX or MAZANOR)
methamphetamine
naltrexone
orlistat (e.g. that which is commercially available as XENICAL)
phendimetrazine (e.g. that which is commercially available as BONTRIL or PLEGINE)
phentermine (e.g. that which is commercially available as FASTIN)
sibutramine (e.g. that which is commercially available as MERIDIA)
a lipid-metabolism improving agent capsaicin
an neuropeptide Y blocker NGD-95-1
kainate/AMPA receptor antagonist
β-adrenergic receptor agonist
compound that reduces caloric intake fat substitute (e.g., that which is commercially available as OLESTRA)
sugar substitute (e.g.. that which is commercially available as ASPARTAME)
anti-diabetes agent insulin glargine (e.g. that which is commercially available as LANTUS)
pioglitazone (e.g. that which is commercially available as ACTOS)
rosiglitazone maleate (e.g. that which is commercially available as AVANDIA)
dietary nutrient sugar
dietary fatty acid
triglyceride
oligosaccharides (e.g., fructo-oligosaccharides, raffinose, galacto-oligosaccharides, xylo-oligosaccharides, beet sugar and soybean oligosaccharides)
protein
vitamin (e.g., vitamin D)
mineral (e.g., calcium, magnesium, phosphorus and iron)

The other therapeutic agents can be made and used at doses as disclosed previously. For example, an anti-osteoporosis agent (see e.g., U.S. Pat. Nos. 2,565,115 and 2,720,483), a non-steroid hormone (see, e.g., U.S. Pat. Nos.

6,121,253; 3,927,197; 6,124,314), a glucagon antagonists (see, e.g., U.S. Pat. No. 5,510,459), a growth hormone secretagogue (see, e.g., U.S. Pat. Nos. 3,239,345; 4,036,979; 4,411,890; 5,206,235; 5,283,241; 5,284,841; 5,310,737; 5,317,017; 5,374,721; 5,430,144; 5,434,261; 5,438,136; 5,494,919; 5,494,920; and 5,492,916; European Patent Nos. 144,230 and 513,974; International Patent Publication Nos. WO 89/07110; WO 89/07111; WO 93/04081; WO 94/07486; WO 94/08583; WO 94/11012; WO 94/13696; WO 94/19367; WO 95/03289; WO 95/03290; WO 95/09633; WO 95/11029; WO 95/12598; WO 95/13069; WO 95/14666; WO 95/16675; WO 95/16692; WO 95/17422; WO 95/17423; WO 95/34311; and WO 96/02530), an agent that increase IGF-1 levels (see, e.g., U.S. Pat. No. 6,166,077), a cytokine (see, e.g., U.S. Pat. No. 4,921,697), a vitronectin receptor antagonist (see e.g., U.S. Pat. No. 6,239,138 and Horton et al., 1991, Exp. Cell Res. 195:368), a bisphosphonate compound (see e.g., U.S. Pat. No. 5,409,911), a kinase inhibitor (U.S. Pat. No. 6,218,410), and an integrin receptor or antagonist thereof (see, e.g., U.S. Pat. No. 6,211,191).

Alternatively, the other therapeutic agents can be made and used at doses as determined empirically.

Therapeutic/Prophylactic Administration and Compositions of the Invention

Due to their activity, the GLP molecules and GLP activators are advantageously useful in human and veterinary medicine. As described above, the compounds of the invention are useful for treating or preventing a bone-related disorder or a nutrition-related disorder in a patient.

When administered to a patient, a GLP molecule or GLP activator is preferably administered as a component of a composition that optionally comprises a to pharmaceutically acceptable carrier or vehicle. In a preferred embodiment, these compositions are administered orally.

Compositions for oral administration might require an enteric coating to protect the composition(s) from degradation within the gastrointestinal tract. In another example, the composition(s) can be administered in a liposomal formulation to shield the GLP molecules and GLP activators disclosed herein from degradative enzymes, facilitate the molecule's transport in the circulatory system, and effect delivery of the molecule across cell membranes to intracellular sites.

GLP molecules and GLP activators intended for oral administration can be coated with or admixed with a material (e.g., glyceryl monostearate or glyceryl distearate) that delays disintegration or affects absorption of the GLP molecule in the gastrointestinal tract. Thus, for example, the sustained release of a GLP molecule can be achieved over many hours and, if necessary, the GLP molecule can be protected from being degraded within the gastrointestinal tract. Taking advantage of the various pH and enzymatic conditions along the gastrointestinal tract, pharmaceutical compositions for oral administration can be formulated to facilitate release of a GLP molecule at a particular gastrointestinal location.

Selectively permeable membranes surrounding an osmotically active driving compound are also suitable for orally administered compositions. Fluid from the environment surrounding the capsule is imbibed by the driving compound, which swells to displace the GLP molecule through an aperture, can provide an essentially zero order delivery profile instead of the spiked profiles of immediate release formulations. A time delay material such as, but not limited to, glycerol monostearate or glycerol stearate can also be used.

Suitable pharmaceutical carriers also include starch, glucose, lactose, sucrose, gelatin, saline, gum acacia, talc, keratin, urea, malt, rice, flour, chalk, silica gel, sodium stearate, glycerol monostearate, talc, sodium chloride, dried skim milk, glycerol, propylene, glycol, water, and ethanol. If desired, the carrier, can also contain minor amounts of wetting or emulsifying agents, or pH buffering agents. In addition, auxiliary, stabilizing, thickening, lubricating, and coloring agents may be used. The composition can be formulated as a suppository, with traditional binders and carriers such as triglycerides.

A pharmaceutical composition comprising a GLP molecule or GLP activator can be administered via one or more routes such as, but not limited to, oral, intravenous infusion, subcutaneous injection, intramuscular, topical, depo injection, implantation, time-release mode, and intracavitary. The pharmaceutical composition is formulated to be compatible with its intended route of administration. Examples of routes of administration include parenteral, e.g., intravenous, intramuscular, intraperitoneal, intracapsular, intraspinal, intrastemal, intratumor, intranasal, epidural, intra-arterial, intraocular, intraorbital, intradermal, subcutaneous, oral (e.g., inhalation), transderrnal (topical— particularly to the ears, nose, eyes, or skin), transmucosal (e.g., oral) nasal, rectal, intracerebral, intravaginal, sublingual, submucosal, and transdermal admninistration.

Administration can be via any route known to be effective by a physician of ordinary skill. Parenteral administration, i.e., not through the alimentary canal, can be performed by subcutaneous, intramuscular, intra-peritoneal, intratumoral, intradermal, intracapsular, intra-adipose, or intravenous injection of a dosage form into the body by means of a sterile syringe, optionally a pen-like syringe, or some other mechanical device such as an infusion pump. A further option is a composition that can be a powder or a liquid for the administration in the form of a nasal or pulmonary spray. As a still further option, the administration can be transdennally, e.g., from a patch. Compositions suitable for oral, buccal, rectal, or vaginal administration can also be provided.

In one embodiment, a pharmaceutical composition of the invention is delivered by a controlled-release system. For example, the pharmaceutical composition can be administered using intravenous infusion, an implantable osmotic pump, a transdermal patch, liposomes, or other modes of administration. In one embodiment, a pump can be used (See e.g., Langer, 1990, Science 249:1527–33; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, the compound can be delivered in a vesicle, in particular a liposome (See e.g., Langer, 1990, Science 249:1527–33; Treat et al., 1989, in *Liposomes in the Therapy of Infectious Disease and Cancer*, Lopez-Berestein and Fidler (eds.), Liss, New York, pp. 353–65; Lopez-Berestein, ibid., pp. 317–27; International Patent Publication No. WO 91/04014; U.S. Pat. No. 4,704, 355). In another embodiment, polymeric materials can be used (See e.g., *Medical Applications of Controlled Release*, Langer and Wise (eds.), CRC Press: Boca Raton, Fla., 1974; *Controlled Drug Bioavailability, Drug Product Design and Performance*, Smolen and Ball (eds.), Wiley: New York (1984); Ranger and Peppas, 1953, J. Macromol. Sci. Rev. Macromol. Chem. 23:61; Levy et al., 1985, Science 5228:190; During et al., 1989, Ann. Neurol. 25:351; Howard et al., 1989, J. Neurosurg. 71:105).

In yet another embodiment, a controlled release system can be placed in proximity of the target. For example, a micropump can deliver controlled doses directly into bone or adipose tissue, thereby requiring only a fraction of the systemic dose (See e.g., Goodson, 1984, in *Medical Applications of Controlled Release*, vol. 2, pp. 115–138). In another example, a pharmaceutical composition of the invention can be formulated with a hydrogel (See, e.g., U.S. Pat. Nos. 5,702,717; 6,117,949; 6,201,072).

In one embodiment, it may be desirable to administer the pharmaceutical composition of the invention locally, i.e., to the area in need of treatment. Local administration can be achieved, for example, by local infusion during surgery, topical application (e.g., in conjunction with a wound dressing after surgery), injection, catheter, suppository, or implant. An implant can be of a porous, non-porous, or gelatinous material, including membranes, such as sialastic membranes, or fibers.

In certain embodiments, it may be desirable to introduce the GLP molecules and GLP activators into the central nervous system by any suitable route, including intraventricular, intrathecal, and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant.

In one embodiment, the invention provides for the treatment of a patient using implanted cells that have been regenerated or stimulated to proliferate in vitro or in vivo prior to reimplantation or transplantation into a recipient. Conditioning of the cells ex vivo can be achieved simply by growing the cells or tissue to be transplanted in a medium that has been supplemented with a growth-promoting amount of the combinations and is otherwise appropriate for culturing of those cells. The cells can, after an appropriate conditioning period, then be implanted either directly into the patient or can be encapsulated using established cell encapsulation technology, and then implanted.

The skilled artisan can appreciate the specific advantages and disadvantages to be considered in choosing a mode of administration. Multiple modes of administration are encompassed by the invention. For example, a GLP molecule of the invention can be administered by subcutaneous injection, whereas another therapeutic agent can be administered by intravenous infusion. Moreover, administration of one or more species of GLP, with or without other therapeutic agents, can occur simultaneously (i.e., co-administration) or sequentially. In another embodiment, the periods of administration of a GLP molecule or GLP activator, with or without other therapeutic agents can overlap. For example a GLP molecule or GLP activator can be administered for 7 days and another therapeutic agent can be introduced beginning on the fifth day of GLP treatment. Treatment with the other therapeutic agent can continue beyond the 7-day GLP treatment.

A pharmaceutical composition of a GLP molecule or GLP activator can be administered before, during, and/or after the administration of one or more therapeutic agents. In one embodiment, a GLP molecule or GLP activator can first be administered to stimulate the expression of insulin, which increases sensitivity to subsequent challenge with a therapeutic agent. In another embodiment, a GLP molecule or GLP activator can be administered after administration of a therapeutic agent. In yet another embodiment, there can be a period of overlap between the administration of the GLP molecule or GLP activator and the administration of one or more therapeutic agents.

A pharmaceutical composition of the invention can be administered in the morning, afternoon, evening, or diurnally. In one embodiment, the pharmaceutical composition is administered at particular phases of the circadian rhythm. In a specific embodiment, the pharmaceutical composition is administered in the morning. In another specific embodiment, the pharmaceutical composition is administered at an artificially induced circadian state.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (See e.g., U.S. Pat. No. 5,698,155). Other examples of suitable pharmaceutical carriers are described in *Remington's Pharmaceutical Sciences*, Alfonso R. Gennaro ed., Mack Publishing Co. Easton, Pa., $19^{th}$ ed., 1995, pp. 1447 to 1676, incorporated herein by reference.

Accordingly, the pharmaceutical compositions herein described can be in the form of oral tablets, capsules, elixirs, syrups and the like.

For instance, for oral administration in the form of a tablet or capsule, the active drug component can be combined with an oral, non-toxic, pharmaceutically acceptable, inert carrier such as, but not limited to, lactose, starch, sucrose, glucose, methyl cellulose, magnesium stearate, dicalcium phosphate, calcium sulfate, mannitol, and sorbitol. For oral administration in liquid form, the oral drug components can be combined with any oral, non-toxic, pharmaceutically acceptable carrier such as, but not limited to, ethanol, glycerol, and water. Moreover, suitable binders, lubricants, disintegrating agents and coloring agents can also be incorporated into the mixture. Suitable binders include, but are not limited to, starch, gelatin, natural sugars (e.g., glucose, beta-lactose), corn sweeteners, natural and synthetic gums (e.g., acacia, tragacanth, sodium alginate), carboxymethylcellulose, polyethylene glycol, and waxes. Lubricants useful for an orally administered drug, include, but are not limited to, sodium oleate, sodium stearate, magnesium stearate, sodium benzoate, sodium acetate, and sodium chloride. Disintegrators include, but are not limited to, starch, methyl cellulose, agar, bentonite, and xanthan gum.

Pharmaceutical compositions adapted for oral administration can be provided, for example, as capsules or tablets; as powders or granules; as solutions, syrups or suspensions (in aqueous or non-aqueous liquids); as edible foams or whips; or as emulsions. For oral administration in the form of a tablet or capsule, the active drug component can be combined with an oral, non-toxic, pharmaceutically acceptable, inert carrier such as, but not limited to, lactose, starch, sucrose, glucose, methyl cellulose, magnesium stearate, dicalcium phosphate, magnesium carbonate, stearic acid or salts thereof, calcium sulfate, mannitol, and sorbitol. For oral administration in the form of a soft gelatine capsule, the active drug component can be combined with an oral, non-toxic, pharmaceutically acceptable, inert carrier such as, but not limited to, vegetable oils, waxes, fats, semi-solid, and liquid polyols. For oral administration in liquid form, the oral drug components can be combined with any oral, non-toxic, pharmaceutically acceptable carrier such as, but not limited to, ethanol, glycerol, polyols, and water. Moreover, suitable binders, lubricants, disintegrating agents and coloring agents can also be incorporated into the mixture. Suitable binders include, but are not limited to, starch, gelatin, natural sugars (e.g., glucose, beta-lactose), corn sweeteners, natural and synthetic gums (e.g., acacia, tragacanth, sodium alginate), carboxymethylcellulose, polyethylene glycol, and waxes. Lubricants useful for an orally administered drug, include, but are not limited to, sodium oleate, sodium stearate, magnesium stearate, sodium benzoate, sodium acetate, and sodium chloride. Disintegrators include, but are not limited to, starch, methyl cellulose, agar, bentonite, and xanthan gum.

Orally administered compositions may contain one or more agents, for example, sweetening agents such as, but not limited to, fructose, ASPARTAME and saccharin. Orally administered compositions may also contain flavoring agents such as, but not limited to, peppermint, oil of wintergreen, and cherry. Orally administered compositions may also contain coloring agents and/or preserving agents.

The GLP molecules and GLP activators can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. A variety of cationic lipids can be used in accordance with the invention including, but not limited to, N-(1(2,3-dioleyloxy)propyl)-N,N,N-trimethylammonium chloride ("DOTMA") and dioleylphosphotidylethanolamine ("DOPE"). Such compositions suit the mode of administration.

GLP molecules and GLP activators can also be delivered by the use of monoclonal antibodies as individual carriers to which the GLP molecules and GLP activators can be coupled. The GLP molecules and GLP activators can also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, or polyethyleneoxide-polylysine substituted with palmitoyl residues. Furthermore, the GLP molecules and GLP activators can be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Pharmaceutical compositions adapted for parenteral administration include, but are not limited to, aqueous and non-aqueous sterile injectable solutions or suspensions, which can contain antioxidants, buffers, bacteriostats and solutes that render the pharmaceutical compositions substantially isotonic with the blood of an intended recipient. Other components that can be present in such pharmaceutical compositions include water, alcohols, polyols, glycerine and vegetable oils, for example. Compositions adapted for parenteral administration can be presented in unit-dose or multi-dose containers (e.g., sealed ampules and vials), and can be stored in a freeze-dried (ie., lyophilized) condition requiring the addition of a sterile liquid carrier (e.g., sterile saline solution for injections) immediately prior to use. Extemporaneous injection solutions and suspensions can be prepared from sterile powders, granules and tablets.

Pharmaceutical compositions adapted for transdermal administration can be provided as discrete patches intended to remain in intimate contact with the epidermis for a prolonged period of time. Pharmaceutical compositions adapted for topical administration can be provided as, for example, ointments, creams, suspensions, lotions, powders, solutions, pastes, gels, sprays, aerosols or oils. A topical ointment or cream is preferably used for topical administration to the skin, mouth, eye or other external tissues. When formulated in an ointment, the active ingredient can be employed with either a paraffinic or a water-miscible ointment base. Alternatively, the active ingredient can be formulated in a cream with an oil-in-water base or a water-in-oil base.

Pharmaceutical compositions adapted for topical administration to the eye include, for example, eye drops or injectable pharmaceutical compositions. In these pharmaceutical compositions, the active ingredient can be dissolved or suspended in a suitable carrier, which includes, for example, an aqueous solvent with or without carboxymethylcellulose. Pharmaceutical compositions adapted for topical administration in the mouth include, for example, lozenges, pastilles and mouthwashes.

Pharmaceutical compositions adapted for nasal administration can comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, pharmaceutical compositions adopted for nasal administration can comprise liquid carriers such as, for example, nasal sprays or nasal drops. These pharmaceutical compositions can comprise aqueous or oil solutions of a GLP molecule. Compositions for administration by inhalation can be supplied in specially adapted devices including, but not limited to, pressurized aerosols, nebulizers or insufflators, which can be constructed so as to provide predetermined dosages of the GLP molecule or GLP activator.

Pharmaceutical compositions adapted for rectal administration can be provided as suppositories or enemas. Pharmaceutical compositions adapted for vaginal administration can be provided, for example, as pessaries, tampons, creams, gels, pastes, foams or spray formulations.

Suppositories generally contain active ingredients in the range of 0.5% to 10% by weight. Oral formulations preferably contain 10% to 95% active ingredient by weight. In a preferred embodiment, the composition is formulated in accordance with routine procedures as a pharmaceutical composition adapted for intraturnoral injection, implantation, subcutaneous injection, or intravenous administration to humans.

Typically, pharmaceutical compositions for injection or intravenous administration are solutions in sterile isotonic aqueous buffer. Where necessary, the composition can also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent.

Where the composition is to be administered by infusion, it can be dispensed with an infusion bottle, bag, or other acceptable container, containing sterile pharmaceutical grade water, saline, or other acceptable diluents. Where the composition is administered by injection, an ampule of sterile water for injection or saline can be provided so that the ingredients may be mixed prior to administration.

The GLP molecules and GLP activators and optionally another therapeutic agent are administered at an effective dose. The dosing and regimen most appropriate for patient treatment will vary with the disease or condition to be treated, and in accordance with the patient's weight and with other parameters.

An effective dosage and treatment protocol can be determined by conventional means, comprising the steps of starting with a low dose in laboratory animals, increasing the dosage while monitoring the effects (e.g., histology, disease activity scores), and systematically varying the dosage regimen. Several factors may be taken into consideration by a clinician when determining an optimal dosage for a given patient. Primary among these is the amount of GLP molecule normally circulating in the plasma, which, in the case of a GLP peptide, is approximately 150 pmol/ml in the resting state, and rising to approximately 225 pmol/ml after nutrient ingestion for healthy adult humans (Orskov and Holst, 1987, Scand J. Clin. Lab. Invest. 47:165). Additional factors include, but are not limited to, the size of the patient, the age of the patient, the general condition of the patient, the particular disease being treated, the severity of the disease, the presence of other drugs in the patient, and the in vivo activity of the GLP molecule.

Trial dosages would be chosen after consideration of the results of animal studies and the clinical literature. A person of ordinary skill in the art can appreciate that information such as binding constants and Ki derived from in vitro GLP binding competition assays may also be used in calculating dosages.

A typical effective human dose of a GLP molecule or GLP activator would be from about 10 µg/kg body weight/day to about 10 mg/kg/day, preferably from about 50 µg/kg/day to about 5 mg/kg/day, and most preferably about 100 µg/kg/day to 1 mg/kg/day. As analogs of the GLP molecules and GLP activators disclosed herein can be 2 to 100 times more potent than naturally occurring counterparts, a typical effective dose of such a GLP analog can be lower, for example, from about 100 ng/kg body weight/day to 1 mg/kg/day, preferably 1 µg/kg/day to 500 µg/kg/day, and even more preferably 1 µg/kg/day to 100 µg/kg/day.

In another embodiment, the effective dose of a GLP molecule or a GLP activator is less than 10 µg/kg/day. In yet another embodiment the effective dose of a GLP molecule or GLP activator is greater than 10 mg/kg/day.

The specific dosage for a particular patient, of course, has to be adjusted to the degree of response, the route of administration, the patients weight, and the patient's general condition, and is finally dependent upon the judgment of the treating physician.

Gene Therapy

Gene therapy approaches can also be used in accordance with the present invention to modulate the expression of a GLP molecule or GLP activator and accordingly, to treat or prevent a bone-related disorder or a nutrition-related disorder.

Any of the methods for gene therapy available in the art can be used in accordance with the present invention (See, e.g., Goldspiel et al., 1993, Clin. Pharm. 12:488–505; Grossman and Wilson, 1993, Curr. Opin. Genet. Devel. 3:110–114; Salmons and Gunzberg, 1993, Hum. Gene Ther. 4:129–141; Morgan and Anderson, 1993, Ann. Rev. Biochem. 62:191–217; Mulligan, 1993, Science 260:926–932; Tolstoshev, 1993, Ann. Rev. Pharmacol. Toxicol. 32:573–596; and Clowes et al., 1994, J. Clin. Invest. 93:644–651; Kiem et al., 1994, Blood 83:1467–1473, each of which is incorporated herein by reference).

Long-term effective use of a gene therapy vector to ameliorate disease in large mammals has been demonstrated. For example, administration of an AAV containing a wild-type gene to dogs suffering from Leber congenital amaurosis, a condition that results in blindness due to a mutation of a gene (RPE65) in the retinal pigment epithelium, has successfully corrected the genetic defect (Ackland et al., 2001, Nat. Genet. 28:92). Expression of the wild-type RPE65 gene was confirmed by RT PCR and restoration of function was demonstrated by electrophysiological studies of the retina, as well as by unbiased observational studies of the treated dogs. The treatment was shown to be effective for at least four months.

Intramuscular administration of an AAV encoding for factor IX to treat dogs suffering from hemophilia has also been reported (Herzog et al., 1999, Nat. Med. 5:56). Administration of AAV encoding factor IX was shown to significantly reduce clotting time in treated dogs for 17 months. Thus, such examples demonstrate that gene therapy can be used to restore lost genetic function in a large animal model using treatment methods known in the art.

Gene therapy refers to therapy performed by administering to a patient an expressed or expressible nucleic acid. Gene therapy involves introducing a gene construct to cells in tissue culture or in vivo.

The recipient's cells or heterologous cells can be engineered to express one or more of the GLP molecules and GLP activators or a combination of a GLP molecule or GLP activator and another therapeutic agent. Methods for introduction of nucleic acid sequences encoding GLP molecules or GLP activators (See, e.g., Bell et al., 1983, Nature 304: 5924) to cells in vitro include, but are not limited to, electroporation, lipofection, DEAE-Dextran transfection, calcium phosphate-mediated transfection, liposome-mediated transfer, and viral infection.

Such ex vivo treatment protocols can be used to transfer DNA into a variety of different cell types including, but not limited to, epithelial cells (U.S. Pat. No. 4,868,116; Morgan and Mulligan WO87/00201; Morgan et al., 1987, Science 237:1476–1479; Morgan and Mulligan, U.S. Pat. No. 4,980, 286), endothelial cells (WO89/05345), fibroblasts (Palmer et al., 1987, Proc. Natl. Acad. Sci. 84:1055–1059; Anson et al., 1987, Mol. Biol. Med. 4:11–20; Rosenberg et al., 1988, Science 242:1575–1578; U.S. Pat. No. 4,963,489), lymphocytes (U.S. Pat. No. 5,399,346; Blaese et al., 1995, Science 270:475–480), and hematopoietic stem cells (Lim et al., 1989, Proc. Natl. Acad. Sci. 86:8892–8896; U.S. Pat. No. 5,399,346).

Accordingly, one can use gene therapy to create a cell line that produces any GLP molecule or GLP activator. Additionally, cells can be engineered to produce a GLP molecule or GLP activator alone or in combination with another agent such as, but not limited to, a peptide hormone (e.g., IGF-1, IGF-2 or growth hormone). The cells can be grown as an implant in an experimental animal or in tissue culture using techniques known in the art. Various expression vectors, including viral vectors, suitable for introduction of genetic information into human cells, can be used to incorporate the constructs encoding the GLP molecule or GLP activator and/or the other therapeutic agent. Once altered genetically, the engineered cells can then be administered to a subject using procedures known in the art.

Alternatively, one can use gene therapy to transfect the recipient's cells in vivo. Methods of administering vectors that transfect cells in vivo are known in the art. Formulations of nucleic acid for such in vivo methods can be, but are not limited to, naked DNA; nucleic acid encapsulated into liposomes or liposomes combined with viral envelope receptor proteins (Nicolau et al., 1983, Proc. Natl. Acad. Sci. 80:1068), DNA coupled to a polylysine-glycoprotein carrier complex, and nucleic acid precipitants.

Nucleic acid preparations can be introduced in vivo using any one of the techniques known in the art such as direct injection, electroporation, and particle bombardment. In addition, "gene guns" have been used for gene delivery into cells (Australian Patent No. 9068389).

Synthetic genes which result in the production of a GLP molecule or GLP activator following either in vitro or in vivo transcription and translation can be constructed using techniques well known in the art (See, e.g., Ausubel et al., 1990, Current Protocols in Molecular Biology p. 8.2.8 to 8.2.13.; Ausubel et al., 1995, Short Protocols in Molecular Biology p. 8.8–8.9, John Wiley & Sons Inc.).

A GLP antagonist can be inhibited with a GLP activator (i.e., an inhibitor of a GLP antagonist) with the use of gene therapy (e.g., antisense, ribozyme, triple helix molecules, and/or recombinant antibodies). In this embodiment, introduction of the GLP activator into a patient results in a decrease in the respective GLP-antagonist-gene expression and/or GLP antagonist protein levels. Techniques for the production and use of antisense, ribozyme, and/or triple helix molecules are well known to those of skill in the art, and in accordance with the present invention.

The present invention encompasses vectors comprising a nucleic acid encoding a polypeptide or peptide GLP molecule or GLP activator of the invention. In one embodiment, a nucleic acid encoding a GLP molecule or GLP activator to be introduced for purposes of gene therapy comprises an inducible promoter operably linked to the coding region, such that expression of the nucleic acid can be controlled using an appropriate inducer or inhibitor of transcription. In another embodiment, the vector contains a promoter, which expresses the cloned construct constitutively. In a further embodiment, the promoter can be down-regulated using a suppressor molecule. Alternatively, the vector contains a promoter, such that an inducing molecule initiates or increases expression of the cloned nucleic acid. In a preferred embodiment, the vector contains a cell-specific promoter. In another preferred embodiment, the vector contains a disease-specific promoter, such that expression is largely limited to diseased tissues or tissues surrounding diseased tissues.

Usually, the method of cellular introduction also comprises the transfer of a selectable marker to the cells, after which the cells are placed under selection to isolate the cells that have taken up and that express the transferred gene. These transfected cells can be administered to a patient.

Several methods have been developed for delivering the nucleic acid molecules to target cells or target tissues. Accordingly, the nucleic acid molecules can be delivered in vivo or ex vivo to target cells. In one embodiment, an expression construct can be delivered directly into a patient. In a particular embodiment, the nucleic acid molecules of the GLP molecule or GLP activator can be injected directly into the target tissue or cell derivation site. Alternatively, a patient's cells are first transfected with an expression construct in vitro, after which the transfected cells are administered back into the subject (i.e., ex vivo gene therapy).

In one embodiment, a vector is introduced in vivo such that it is taken up by a cell and directs the transcription of a nucleic acid of the invention. Such a vector can remain episomal or can become chromosomally integrated. Expression vectors can be plasmid, viral, or others known in the art, that can be used to replicate and/or express the cloned nucleotide sequence encoding a GLP nucleic acid in a target mammalian cell. A variety of expression vectors useful for introducing into cells the nucleic acid molecules are well known in the art ( e.g., pCI, pVPack, pCMV, pSG5). Expression constructs can be introduced into target cells and/or tissues of a subject using vectors which including but not limited to, adenovirus, adeno-associated virus, retrovirus and herpes virus vectors, in addition to other particles that introduce DNA into cells, such as liposomes.

In a particular embodiment, the nucleic acid molecules can be introduced into the target tissue as an implant, for example, in a polymer formulation (See, e.g., U.S. Pat. No. 5,702,717). In another embodiment, the nucleic acid molecules can be targeted to the desired cells or tissues.

A nucleic acid sequence can be expressed using any promoter known in the art capable of expression in mammalian, preferably human cells. Such promoters can be inducible or constitutive. These promoters include, but are not limited to, the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. 78:1441–1445), and the regulatory sequences of the metallothionein gene (Brinster et al., 1982, Nature 296:39–42). Tissue-specific promoters include the promoter region of osteocalcin.

In one embodiment, in which recombinant cells are used in gene therapy, nucleic acid sequences encoding polypeptides of the invention are introduced into the cells such that they are expressible by the cells or their progeny, and the recombinant cells are then administered in vivo for therapeutic effect. In a specific embodiment, stem or progenitor cells are used. Any stern and/or progenitor cells which can be isolated and maintained in vitro can potentially be used in accordance with this embodiment of the present invention, such as, but not limited to, hematopoietic cells, neuronal progenitor cells, hepatic progenitor cells, osteoblasts, and fetal stem cells (See, e.g., PCT Publication WO 94/08598; Stemple and Anderson, 1992, Cell 71:973–985; Pittelkow and Scott, 1986, Mayo Clinic Proc. 61:771; Rheinwald, 1980, Meth Cell Bio. 21A:229).

In other embodiments, the nucleic acid of the invention can include other appended groups such.as peptides (e.g., for targeting host cell receptors in vivo), or agents facilitating transport across the cell membrane (see, e.g., Letsinger et al., 1989, Proc. Natl. Acad. Sci. 86:6553–6556; Lemaitre et al., 1987, Proc. Natl. Acad. Sci. 84:648–652; PCT Publication No. WO 88/09810) or the blood-brain banier (See, e.g., PCT Publication No. WO 89/10134). For example, PCT Publication No. WO 88/09810 discloses nucleic acid conjugates comprising a relatively short oligonucleotide sequence, a linking group, and group which modifies the hydrophilic lipophilic balance to provide an amphiphillic product that aids in the transport of the conjugate across the cellular membrane. Another exanple, PCT Publication No. WO 89/10134, discloses chimeric peptides which are adapted to deliver a neuropharmaceutical agent, conjugated with a transportable peptide, into the brain by transcytosis across the blood-brain barrier. In addition, oligonucleotides can be modified with hybridization-triggered cleavage agents (See, e.g., Krol et al., 1988, BioTech. 6:958–976) or intercalating agents (See, e.g., Zon, 1988, Pharm. Res. 5:539–549). To this end, the oligonucleotide can be conjugated to another molecule, e.g., a peptide, hybridization triggered cross-linking agent, transport agent, or hybridization-triggered cleavage agent.

The nucleic acid molecules can be inserted into vectors and used as gene therapy vectors. Gene therapy vectors can be delivered to a subject by, for example, intravenous injection, local administration (U.S. Pat. No. 5,328,470) or by stereotactic injection (See, e.g., Chen et al., 1994, Proc. Natl. Acad. Sci. 91:3054–3057). The pharmaceutical preparation of the gene therapy vector can include the gene therapy vector in an acceptable diluent, or can comprise a slow release matrix in which the vector is imbedded. Alternatively, where the vector can be produced intact from recombinant cells, e.g., retroviral vectors, the pharmaceutical preparation can include one or more cells producing the vector.

Any type of plasmid, cosmid, YAC or viral vector can be used to prepare the recombinant construct. Alternatively, vectors can be used which selectively target a tissue or cell type, e.g., viruses that infect bone cells. Further specificity can be realized by using a tissue-specific or cell-specific promoter in the expression vector.

In a specific embodiment, an expression vector is administered directly in vivo, where the vector is expressed to produce the encoded product. This can be accomplished by any of numerous methods known in the art, e.g., by placing a nucleic acid of the invention in an appropriate expression vector such that, upon administration, the vector becomes intracellular and expresses a nucleic acid of the invention. Such vectors can be internalized by using, for example, a defective or attenuated retroviral vector or other viral vectors that can infect mammalian cells (See e.g., U.S. Pat. No. 4,980,286).

Alternatively, an expression construct containing a nucleic acid of the invention can be injected directly into a target tissue as naked DNA. In another embodiment, an expression construct containing a nucleic acid of the invention can be introduced into a cell using microparticle bombardment, for example, by using a Biolistic gene gun (DuPont, Wilmington, Del.). In another embodiment, an expression construct containing a nucleic acid of the invention can be coated with lipids, or cell-surface receptors, or transfecting agents, such that encapsulation in liposomes, microparticles, or microcapsules facilitates access to target tissues and/or entry into target cells.

In yet another embodiment, an expression construct containing a nucleic acid of the invention is linked to a polypeptide that is internalized in a subset of cells or is targeted to a particular cellular compartment. In a further embodiment, the linked polypeptide is a nuclear targeting sequence that targets the vector to the cell nucleus. In another further embodiment, the linked polypeptide is a ligand that is internalized by receptor-mediated endocytosis in cells expressing the respective receptor for the ligand (See e.g., Wu and Wu, 1987, J. Biol. Chem. 262:4429–4432).

In another embodiment, nucleic acid-ligand complexes can be formed such that the ligand comprises a fusogenic viral peptide, which disrupts endosomes, thereby allowing the nucleic acid to avoid lysosomal degradation. In another embodiment, a nucleic acid of the invention can be targeted in vivo via a cell-specific receptor resulting in cell-specific uptake and expression (See e.g., International Patent Publications WO 92/06180, WO 92/22635, WO 92/20316, and WO 93/14188). For example, WO 92/06180 discloses that a virus or cell can be targeted to a target cell for internalization in vivo by introducing a receptor-specific molecule onto the surface of the virus or cell to produce a modified virus or cell which specifically binds to a receptor on the surface of the target cell, resulting in internalization by the target cell. Another example, WO 93/14188, discloses the use of a genetically engineered retroviral packaging cell line that has altered the viral envelope such that it contains a peptide that will bind to a molecule on the membrane of the target cell for the transfer of genetic information Still other examples, WO 92/22635 and WO 92/20316, disclose a molecular complex for targeting a gene to a specific cell in vivo comprising an expressible gene complexed to a carrier that is a conjugate of a gene binding agent and a cell-specific binding agent, which is specific for a receptor that mediates internalization of bound ligands by endocytosis.

In yet another embodiment, a nucleic acid of the invention is introduced intracellularly and, by homologous recombination, can transiently or stably be incorporated within the host cell DNA, which then allows for its expression, (Koller and Smithies, 1989, Proc. Natl. Acad. Sci. 86:8932–8935; Zijlstra et al., 1989, Nature 342:435–438).

In one embodiment, viral vectors are used that contain nucleic acids encoding compounds that activate cytokine receptors (i.e., cytokines or antibodies), or compounds that activate molecules expressed on activated immune cells (See, e.g., Miller et al., 1993, Meth. Enzymol. 217:581–599). In a specific embodiment, a viral vector that contains nucleic acid sequences encoding 4-1BB ligand, or anti-4-1BB immunoglobulin, and/or IL-12 are used. For example, a retroviral vector can be used in which sequences not necessary for packaging of the viral genome and integration into host cell DNA have been deleted, and nucleic acid sequences encoding 4-1BB ligand, or anti-4-1BB immunoglobulin, or IL-12 are cloned into the vector, thereby facilitating delivery of the transgene into a subject. Greater detail about retroviral vectors is available in Boesen et al., 1994, Biotherapy 6:291–302, which describes the use of a retroviral vector to deliver the mdr1 gene to hematopoietic stem cells.

Other viral vectors can be used for gene therapy approaches in accordance with the invention. For example, adenoviruses are useful for delivering gene constructs to respiratory epithelia. Other targets for adenovirus-based delivery systems are the liver, the central nervous system, endothelial cells, and muscle cells. Moreover, adenoviruses are able to infect non-dividing cells (See, e.g., Rosenfeld et al., 1991, Science 252:431–434; Rosenfeld et al., 1992, Cell 68:143–155; Mastrangeli et al., 1993, J. Clin. Invest. 91:225–234; Kozarsky and Wilson, 1993, Curr. Opin. Genet. Develop. 3:499–503; Bout et al., 1994, Hum. Gene Ther. 5:3–10; PCT Publication No. WO 94/12649; and Wang et al., 1995, Gene Ther. 2:775–783).

Accordingly, adeno-associated virus can also be used in the gene therapy approaches of the present invention (See, e.g., Walsh et al., 1993, Proc. Soc. Exp. Biol. Med. 204:289–300; U.S. Pat. No. 5,436,146).

In this embodiment, the nucleic acid is introduced into a cell prior to administration in vivo of the resulting recombinant cell. Such introduction can be carried out by any method known in the art, including, but not limited to, transfection, electroporation, microinjection, infection with a viral or bacteriophage vector containing the nucleic acid sequences, cell fusion, chromosome-mediated gene transfer, microcell-mediated gene transfer, and spheroplast fusion. Numerous techniques are known in the art for the introduction of foreign genes into cells (See, e.g., Maniatis et al., 1989; Current Protocols, 2000; Loeffler and Behr, 1993, Meth. Enzymol. 217:599–618; Cohen et al., 1993, Meth. Enzymol. 217:618–644; Cline, 1985, Pharmacol. Ther. 29:69–92) and can be used in accordance with the present invention. In a preferred embodiment, the technique stably transfers a nucleic acid of the invention to a target cell, such that the nucleic acid is inherited by the cell's progeny.

The resulting recombinant cells can be delivered to a subject by various methods known in the art, and the skilled artisan would appreciate appropriate modes of administration. For example, intravenous administration may be the preferred mode of administration for recombinant hematopoietic stem cells. The number of recombinant cells to be administered to a subject can be determined by one skilled in the art, and would include a consideration of factors such as the desired effect, the disease state, and the mode of administration.

Cells into which a nucleic acid of the invention can be introduced for purposes of gene therapy include, but are not limited to, epithelial cells, endothelial cells, keratinocytes, fibroblasts, muscle cells, hepatocytes, blood cells (e.g., B lymphocytes, T lymphocytes, eosinophils, granulocytes, macrophages, megakaryocytes, monocytes, neutrophils), stem cells or progenitor cells (e.g., undifferentiated cells obtained from adipose, bone marrow, blood, fetal liver, and umbilical cord (See, e.g., Rheinwald, 1980, Meth. Cell Bio. 21A:229; International Publication No. WO 94/08598; Pittelkow and Scott, 1986, Mayo Clinic Proc. 61:771; and Stemple and Anderson, 1992, Cell 71:973–985). The cells used for introduction of a nucleic acid of the invention can be autologous or non-autologous. In a preferred embodiment, the cells used for gene therapy are autologous to the subject.

One skilled in the art will appreciate that many different promoters can be used to drive expression of a nucleic acid of the invention. In one embodiment, the promoter comprises hormone-sensitive elements. For example, a promoter containing an androgen-sensitive enhancer would be activated to a greater degree in androgen-producing cells or adjacent tissues. Such an expression construct may be beneficial for targeting tissues secreting abnormally high levels of androgen. In another embodiment, the promoter comprises elements of a fibroblast-specific promoter. In a further embodiment, the fibroblast-specific promoter comprises promoter elements from synovial fibroblasts. Alternatively, the promoter comprises elements of promoters that are activated in aggressive rheumatoid arthritis synovial fibroblasts. In a particular embodiment, the promoter comprises a portion of a proglucagon promoter. In a non-limiting example, a viral vector is used in which the viral promoter is replaced fully, or in part, with at least parts of a proglucagon promoter. Such an expression construct would more specifically be expressed in proglucagon-expressing cells.

Gene therapy approaches can also be used in accordance with the present invention to inhibit antagonists of GLP, particularly DPP-IV. For example, ribozyme and triple helix molecules can be used to target gene products of a GLP inhibitor, or of an aberrant GLP gene, resulting in a decrease in GLP inhibitor protein or aberrant GLP protein. Techniques for the production and use of antisense ribozyme and/or triple helix molecules are well known to those of skill in the art and can be designed with respect to the nucleotide sequence encoding the amino acid sequence of the target gene, also known in the art.

In another embodiment, mutations can be introduced into the gene encoding the GLP receptor resulting in an altered sequence that activates the receptor thus simulating increased GLP receptor binding (U.S. Pat. No. 6,077,949). The application of automated gene synthesis techniques provides an opportunity for generating sequence variants of the naturally occurring GLP receptor gene. The skilled artisan can appreciate that polynucleotides coding for variants of the GLP receptor can be generated by substitution of codons for those represented in the naturally occurring polynucleotide sequences provided herein. In addition, polynucleotides coding for synthetic variants of the GLP receptor herein provided can be generated which incorporate from 1 to 20, e.g. from 1 to 5, amino acid substitutions, or deletions or additions. The modified GLP receptor can be placed in an expression vector and administered to a subject in need of treatment to increase receptor activity in a desired tissue.

Antisense Therapy

In one embodiment, an antisense approach to gene therapy can be used to treat a bone-related disorder or a nutrition-related disorder. Antisense approaches to gene therapy involve the use of riboprobes that can hybridize to a portion of the target mRNA. Additionally, non-ribose antisense constructs are contemplated in the present invention including, but not limited to, peptide nucleic acids (PNA), LNA, phosphine analogues, phosphotionates, and PEGA modified antisense constructs. Preventing transcription of a GLP antagonist will enhance GLP activity. The skilled artisan will recognize that absolute complementarity is not required, such that some degree of mismatch can result in, at least, transitory duplex formation. In one non-limiting example, the antisense riboprobe binds to the target mRNA transcript and prevents its translation. In one embodiment, the target mRNA encodes a GLP antagonist. In another embodiment, the target mRNA is an aberrant GLP mRNA.

Riboprobes that are complementary to the 5' untranslated sequences, up to and including the AUG initiation codon, can be used effectively to inhibit translation of a GLP mRNA. Riboprobes complementary to the 3' untranslated sequences of mRNAs also can be effective at inhibiting GLP mRNA translation (See, e.g., Wagner, 1994, Nature 372:333–335). Moreover, antisense riboprobes complementary to mRNA coding regions can be used in accordance with the invention.

Preferably, in vitro studies are performed to assess the ability of an antisense riboprobe to inhibit gene expression. These studies typically use controls which distinguish between antisense-mediated inhibition of gene expression and nonspecific biological effects of riboprobes. Preferably, these studies compare antisense-mediated changes in the levels of the target RNA or target protein with levels of an internal control RNA or protein.

In one embodiment, a recombinant DNA construct comprising an antisense riboprobe under the control of a pol III or pol II promoter is used to generate antisense riboprobes in a cell. The use of such a construct to transfect target cells in the subject can result in the transcription of sufficient amounts of a riboprobe to reduce or inhibit mRNA and/or protein expression. In one embodiment, the mRNA is a GLP inhibitor mRNA. In another embodiment, the mRNA is an aberrant GLP mRNA. Low transfection rates or low transcription activity of the DNA construct can nevertheless generate sufficient antisense molecules to demonstrate clinical effectiveness.

In another embodiment, a GLP inhibitor antisense nucleic acid sequence, or an aberrant GLP antisense nucleic acid sequence, is cloned into an expression vector, preferably a mammalian expression vector.

In another embodiment, aberrant GLP or GLP inhibitor antisense nucleic acid molecules of the invention are cloned into a vector, which is designed to target the vector (and thereby target expression of the antisense riboprobe) to specific tissues or cell-types. For example, an antisense riboprobe can be linked to peptides or antibodies that specifically bind receptors or antigens expressed on the target cell surface, thereby targeting the vector to the cells.

In another embodiment, the vector comprises a promoter that is more highly activated in diseased cells or tissues, as compared to normal cells or tissues.

Ribozyme Therapy

Ribozyme therapy can be used to treat a bone-related disorder, a nutrition-related disorder.

Ribozymes are enzymatic RNA molecules capable of catalyzing the specific cleavage of a single-stranded nucleic acid, such as an mRNA (See, e.g., Rossi, 1994, Curr. Biol. 4:469–471). The mechanism of ribozyme action involves sequence-specific hybridization of the ribozyme molecule to complementary target RNA, followed by an endonucleolytic cleavage. The composition of ribozyme molecules include one or more sequences complementary to the target gene mRNA, and catalytic sequences responsible for mRNA cleavage (see e.g., U.S. Pat. No. 5,093,246 which is incorporated by reference in its entirety). Thus, ribozymes (e.g., hammerhead ribozymes) can be used to catalytically cleave mRNA transcripts thereby inhibiting the expression of a protein encoded by a particular mRNA (See, e.g., Haselhoff and Gerlach, 1988, Nature 334:585–591). A ribozyme having specificity for a nucleic acid molecule encoding a polypeptide of the invention can be designed based upon the nucleotide sequence of the nucleic acid molecules of the invention. Accordingly, in one embodiment, an engineered hammerhead motif ribozyme molecule specifically and efficiently catalyzes endonucleolytic cleavage of RNA sequences encoding a GLP antagonist of the invention.

In another embodiment, an mRNA encoding a polypeptide of the invention is used to select a catalytic RNA having a specific ribonuclease activity from a pool of RNA molecules (See, e.g., Bartel and Szostak, 1993, Science 261:1411–1418).

Specific ribozyme cleavage sites within a potential RNA target are identified by scanning the molecule of interest for ribozyme cleavage sites, which include the sequences GUA, GUU and GUC. Once identified, short RNA sequences of approximately 15 to 20 ribonucleotides corresponding to a cleavage site of a target gene are evaluated for predicted structural features, such as secondary structure, that may make the oligo-nucleotide suitable. The suitability of candidate sequences also can be evaluated by testing their ability to hybridize with complementary oligonucleotides, using for example, ribonuclease protection assays.

Triple-Helix Therapy

In one embodiment, nucleic acid molecules that form triple helical structures are used to treat a bone-related disorder or a nutrition-related disorder. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells (See, e.g., Helene, 1991, Antican. Drug Des. 6:569–584; Helene, 1992, Ann. N.Y. Acad. Sci. 660:27–36; Maher, 1992, Bioassays 14:807–815).

Nucleic acid molecules to be used to inhibit transcription by triple helix formation can be single stranded oligonucleotides. The base composition of these oligonucleotides can be designed to promote triple helix formation via Hoogsteen base pairing rules, preferably with long stretches of purines or pyrimidines on one strand of the duplex. Nucleotide sequences can be pyrimidine-based thereby resulting in TAT and CGC+triplet across the three associated strands of the resulting triple helix. The pyrimidine-rich molecules provide base complementarity to a purine-rich region of a single strand of the duplex in a parallel orientation to that strand. Purine-rich nucleic acid molecules also can be chosen, for example, containing a stretch of guanine residues. These molecules can form a triple helix with a DNA duplex that is rich in GC pairs, in which most of the purine residues are located on a single strand of the targeted duplex, resulting in GGC triplets across the three strands in the triplex.

Additionally, the number of potential sequences that can be targeted for triple helix formation can be increased by creating a "switchback" nucleic acid molecule. Switchback molecules are synthesized in an alternating 5'-3', 3'-5' manner, such that the molecule first hybridizes with one strand of a duplex, followed by hybridization with another strand, thus eliminating the requirement for a stretch of purines or pyrimidines on one strand of a duplex.

Ribozyme and triple helix molecules of the invention can be prepared by any method known in the art for the synthesis of DNA or RNA molecules (e.g., oligodeoxyribonucleotides or oligoribonucleotides). Such methods include, for example, solid phase phosphoramidite chemical synthesis.

These oligonucleotides can be administered directly, for example, via injection. Alternatively, RNA molecules can be generated in vitro or in vivo by transcription of DNA sequences. Such DNA sequences can be incorporated into a wide variety of vectors known in the art that feature a suitable RNA polymerase promoter such as, for example, a T7 or SP6 polymerase promoter. In a preferred embodiment, a bone-cell specific promoter is used to produce an expression vector comprising a nucleic acid sequence of the invention. In another preferred embodiment, a bone-specific promoter is used to produce an expression vector comprising a nucleic acid sequence of the invention.

Antibody Therapy

The invention also encompasses the use of antibody therapy to treat a bone-related disorder or a nutrition-related disorder. In one embodiment, nucleic acid molecules comprising sequences encoding antibodies that bind to a GLP antagonist are administered via gene therapy. In a particular embodiment, recombinant cells are used that contain nucleic acid sequences encoding antibodies to GLP antagonist polypeptides of the invention. The gene construct is expressed such that the recombinant antibody is secreted or expressed on the cell surface. The recombinant cells are then administered in vivo for therapeutic effect.

GLP antibodies of the invention, including antibodies conjugated to therapeutic moieties, can be administered to an individual alone or in combination with an anti-osteoporosis agent, anti-obesity agent, growth factor or hormone. In one embodiment, an antibody directed to a GLP inhibitor polypeptide is administered first, followed by an anti-osteoporosis agent, anti-obesity agent, growth factor, or hormone within 24 hours. The treatment cycle can be repeated if warranted by the clinical response of the patient. Furthermore, the antibody, anti-osteoporosis agent, growth factor, or hormone can be administered via separate routes, such as for example, by intravenous and intramuscular administration.

Still another aspect of the invention is a pharmaceutical composition. comprising an antibody of the invention and a pharmaceutically acceptable carrier. In preferred embodiments, the pharmaceutical composition contains an antibody of the invention, a GLP molecule, and a pharmaceutically acceptable carrier.

Vaccine Therapy

Vaccine therapy can be used to treat a bone-related disorder or a nutrition-related disorder. Vaccine therapy can be administered to a subject in need of such treatment, e.g., a subject expressing an aberrant GLP variant or an aberrant intermediate in the GLP cascade. The nucleotides of the invention, including variants and derivatives, can be used as vaccines, e.g., by genetic immunization. Genetic immunization is particularly advantageous as it stimulates a cytotoxic T-cell response but does not utilize live attenuated vaccines, which can revert to a virulent form and infect the host causing the very infection sought to be prevented. As used herein, genetic immunization comprises inserting the nucleotides of the invention into a host, such that the nucleotides are taken up by cells of the host and the proteins encoded by the nucleotides are translated. These translated proteins are then either secreted or processed by the host cell for presentation to immune cells and an immune reaction is stimulated. Preferably, the immune reaction is a cytotoxic T cell response; however, a humeral response or macrophage stimulation is also useful in preventing future infections. The skilled artisan will appreciate that there are various methods for introducing foreign nucleotides into a host animal and subsequently into cells for genetic immunization, for example, by intramuscular injection of about 50 mg of plasmid DNA encoding the proteins of the invention solubilized in 50 ml of sterile saline solution, with a suitable adjuvant (See, e.g., Weiner and Kennedy, 1999, Sci. Am. 7:50–57; Lowrie et al., 1999, Nature 400:269–271).

Kits

The invention also encompasses kits for detecting the presence of a polypeptide or nucleic acid of the invention in a biological sample (a test sample). Such kits can be used to determine if a subject is suffering from or is at increased risk of developing a disorder associated with aberrant expression of a polypeptide of the invention as discussed, for example, in sections above relating to uses of the pharmaceutical compositions of the invention.

For example, kits can be used, to determine if a subject is suffering from or is at increased risk of developing a bone-related disorder or a nutrition-related disorder.

In another example, kits can be used to determine if a subject is suffering from or is at risk for disorders that are associated with aberrant expression of a polypeptide of the invention.

The kit, for example, can comprise a labeled compound or agent capable of detecting the polypeptide or mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for observing that the tested subject is suffering from or is at risk of developing a disorder associated with aberrant expression of the polypeptide if the amount of the polypeptide or mRNA encoding the polypeptide is above or below a normal level.

For antibody-based kits, the kit can comprise, for example: (1) a first antibody (e.g., attached to a solid support) which binds to a GLP polypeptide; and, optionally, (2) a second, different antibody which binds to either the polypeptide or the first antibody and is conjugated to a detectable agent.

For oligonuclcotide-based kits, the kit can comprise, for example: (1) an oligonucleotidc, e.g., a detectably labeled oligonucleotide, which hybridizes to a nucleic acid sequence encoding a polypeptide of the invention or (2) a pair of primers useful for amplifying a nucleic acid molecule encoding a polypeptide of the invention. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

The invention provides a kit containing an antibody of the invention conjugated to a detectable substance, and instructions for use.

The pharmaceutical compositions of the invention can be included in a container, pack, or dispenser together with instructions for administration.

Diagnostic and Monitoring Assays

The methods described herein can furthermore be utilized as diagnostic assay or an assay to monitor disorder progression or treatment effectiveness. For example, the assays described herein can be utilized to identify a subject having or at risk of developing a disorder associated with aberrant expression or activity of a GLP molecule. Alternatively, the assays can be utilized to identify a subject having or at risk for developing such a disease or disorder. Thus, the present invention provides a method in which a test tissue sample is obtained from a subject and a GLP molecule is detected, wherein the presence of the GLP molecule is diagnostic for a subject having or at risk of developing a disease or disorder associated with aberrant expression or activity of the GLP molecule. As used herein, a "test tissue sample" refers to a biological sample obtained from a subject of interest. For example, a test sample can be a biological fluid (e.g., serum), cell sample, or tissue (eg., bone or adipose).

Furthermore, the assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant expression or activity of a GLP molecule. For example, such methods can be used to determine whether a subject can be effectively treated with a specific agent or class of agents (e.g., agents of a type which increase activity of the GLP mlecule). Thus, the present invention provides methods for determining whether a subject can be effectively treated with an agent for a disorder associated with aberrant expression or activity of a GLP molecule in which a test tissue sample is obtained and the GLP molecule is detected (e.g., wherein the presence of the polypeptide or nucleic acid is diagnostic for a subject that can be administered the agent to treat a disorder associated with aberrant expression or activity of the GLP mlecule).

The methods of the invention can also be used to detect genetic lesions or mutations in a gene encoding a GLP molecule, thereby determining if a subject with the lesioned gene is at risk for a disorder characterized aberrant expression or activity of a GLP molecule. In preferred embodiments, the methods include detecting, in a sample of cells from the subject, the presence or absence of a genetic lesion or mutation characterized by at least one of an alteration affecting the integrity of a gene encoding the GLP molecule, or the mis-expression of the gene encoding the GLP molecule. For example, such genetic lesions or mutations can be detected by ascertaining the existence of at least one of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of a the protein encoded by the gene; 9) an allelic loss of the gene; and 10) an inappropriate post-translational modification of the protein encoded by the gene. As described herein, there are a large number of assay techniques known in the art which can be used for detecting lesions in a gene.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al., 1988, *Science* 241:1077–1080; and Nakazawa et al., 1994, *Proc. Natl. Acad. Sci. USA* 91:360–364), the latter of which can be particularly useful for detecting point mutations in a gene (see, e.g., Abravaya et al., 1995, *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to the selected gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al., 1990, *Proc. Natl. Acad. Sci. USA* 87:1874–1878), transcriptional amplification system (Kwoh, et al.,1989, *Proc. Natl. Acad Sci. USA* 86:1173–1177), Q-Beta Replicase (Lizardi et al., 1988, *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a selected gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

The effectiveness of the methods of treatment of the invention on a patient can be evaluated by, for example, determining the level of one or more markers of bone resorption as indicative of GLP activity. Thus, changes in the level of the markers of bone resorption after GLP molecule or activator administration can monitor treatment effectiveness. In one embodiment, the marker of bone resorption is a C-terminal telopeptide of type I collagen (S-CTX) and/or degradation products thereof (Rosenquist et al., 1998, Clin. Chem. 44:2281–2289; Christgau et al., 1998, Clin. Chem. 44:2290–2300). The level of a marker of bone resorption can be determined using methods known in the art (e.g., ELISA; Serun CrossLaps™). In a particular embodiment, a decrease in the level of circulating S-CTX indicates that the GLP treatment of a patient is effective. In accordance with the methods of the invention, measurement of a marker of bone resorption can be used to determine the optimal dosage of a therapeutic agent for treating a bone-related disorder.

The present invention may be better understood by reference to the following non-limiting Examples, which are provided only as exemplary of the invention. The following examples are presented to more fully illustrate the preferred embodiments of the invention. They should in no way be construed, however, as limiting the broader scope of the invention.

EXAMPLES

In these Examples, hematology and serum chemistry including glucose were measured using an auto analyzer (Vitros). Serum FSI-I was measured by IRMA (Coat-A-Count®, DPC, Los Angeles, Calif.). Serum C-telopeptide fragments of collagen type I degradation (S-CTX) were measured by ELISA, Serum CrossLaps™ assay (Osteometer BioTech A/S-Denmark). Serum osteocalcin was determined by ELISA, an assay which determines the N-terminal mid segment of the molecule. Serum insulin and c-peptide were both assessed by RIA (Coat-A-Count® for insulin and Double Antibody C-peptide for c-peptide both DPC, Los Angeles, Calif.).

Example 1

Effect of Oral Fructose on GLP-1, GIP, and Rate of Bone Resorption

Twelve healthy women (ages 30–45) and men (ages 30–60) were included in a randomized, controlled crossover study comparing the effects of oral fructose on GLP-1, on GIP and on bone turnover. Bone turnover was assayed by measuring the amount of S-CTX in a subject's serum. Briefly, an immunoassay was performed using monoclonal antibodies specific to S-CTX fragments generated exclusively from collagen type I degradation during resorption of mature bone tissue (Rosenquist et al., 1998, Clin. Chem. 44:2281–2289). The individuals had no medical history of diseases related to bone turnover such as cancer, rheumatoid arthritis or diseases compromising absorption from the gut or excretion/re-absorption from the kidney, or any other serious disease that might influence the conduct of the study. A general laboratory screening including hematology and serum chemistry gave no indication of specific organ dysfunction. The individuals had not taken any medication that would effect bone metabolism, such as, calcium, vitamin D, estrogen or progestin in any administration form for more than 3 months prior to the beginning of the study. Subjects had never been treated with bisphosphonates or fluoride.

Sampling

Subjects fasted from 10 p.m. the evening prior to the experiment and initial blood samples were collected between 7:30 am. and 8:30 a.m. Immediately thereafter, oral fructose was initiated. Blood samples were collected at precisely 1, 2, 3, 6 and 9 hours after the first blood sample was drawn. A washout period of 2 weeks was instituted between each experiment.

Interventions

Oral fructose consisted of 75 g fructose dissolved in 300 ml water with the juice of a half lemon added. Oral fructose induced a reduction of 36% in S-CTX after 2 hours (FIG. 1A) whereas the level of GLP-1 was doubled to 220% after 2 hours, compared to the baseline of 100% at $T_0$. Accordingly, the occurrence of the other fragments of proglucagon doubled, as did GLP-1. The level of GIP was almost maintained at baseline. Following oral fructose administration, the concentration of GLP-1 rises, as S-CTX, a marker of bone resorption, decreases. GLP-1 can be useful for decreasing bone resorption and for treating or preventing osteoporosis.

Example 2

Effect of Oral Long Chained Fatty Acids on GLP-1, GIP, and Bone Resorption Rate

Twelve healthy women (ages 30–45) and men (ages 30–60) with the same in- and exclusion-criteria as in Example 1 were included in a randomized, controlled crossover study comparing the effects of oral long-chained fatty acids (LCFA) on GLP-1, on GIP and on bone turnover. Bone turnover was assayed by measuring the amount of S-CTX in a subject's serum. Briefly, an imunoassay was performed using monoclonal antibodies specific to S-CTX fragments generated exclusively from collagen type I degradation during resorption of mature bone tissue (Rosenquist et al., 1998, Clin. Chem. 44:2281–2289).

Sampling

Subjects fasted from 10 p.m. the evening prior to the experiment and initial blood samples were collected between 7:30 a.m. and 8:30 a.m. Immediately thereafter oral LCFA were administered. Blood samples were collected at precisely 1, 2, 3, 6 and 9 hours after the first blood sample was drawn. A washout period of 2 weeks was instituted between each experiment.

Interventions

Figure 1B:
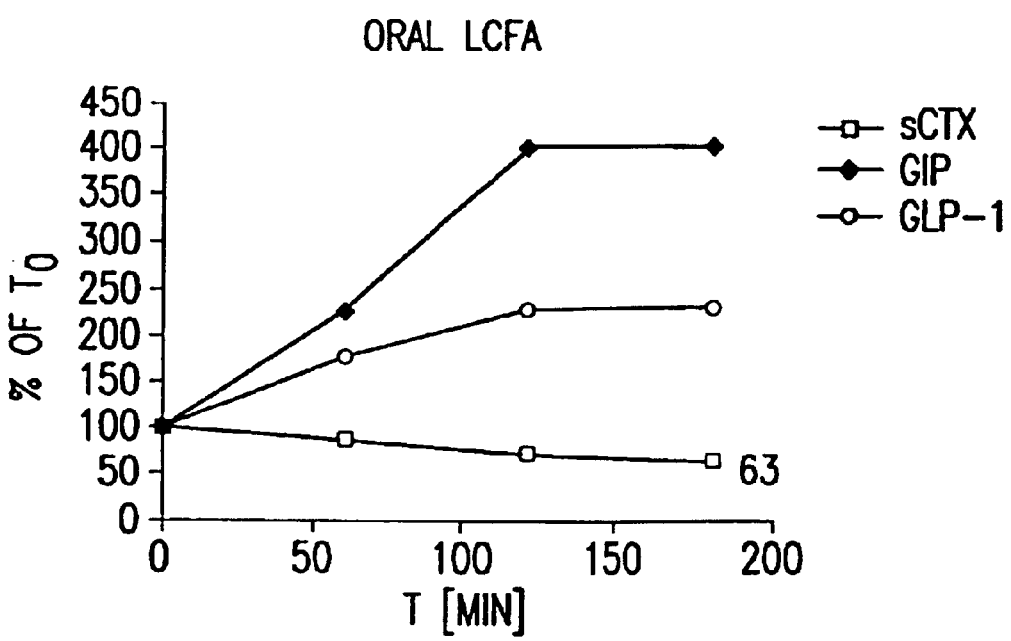

Oral LCFA consisted of 70 ml emulsion of long chained fatty acids (Calogen). Oral LCFA induced a reduction of 37% in S-CTX after 3 hours (FIG. 1B) and the occurrence of GLP-1 was doubled to the level of 230% after 3 hours compared to the baseline of 100% at T0. These results are very similar to the equivalent data of Example 1. However, the occurrence of GIP was increased significantly to the level of 400%. Comparison with the level of GIP in Example 1, indicates that GIP has little or no influence on bone resorption. Following oral LCFA administration, the concentration of GLP-1 rises as S-CTX, a marker for bone resorption decreases. GLP-1 can be useful for decreasing bone resorption and for treating or preventing osteoporosis.

Example 3

Effect of Oral Protein on GLP-2, GIP, and Bone Resorption Rate

Twelve healthy women (ages 30–45) and men (ages 30–60) with the same in- and exclusion-criteria as in Example 1 were included in a randomized, controlled crossover study comparing the effects of oral protein on GLP-2, on GIP, and on bone turnover. Bone turnover was assayed by measuring the amount of S-CTX in a subject's serun. Briefly, an imunoassay was performed using monoclonal antibodies specific to S-CTX fragments generated exclusively from collagen type I degradation during resorption of mature bone tissue (Rosenquist et al., 1999, Clin. Chem. 44:2281–2289).

Sampling

Subjects fasted from 10 p.m. the evening prior to the experiment and initial blood samples were collected between 7:30 a.m. and 8:30 a.m. Immediately thereafter, protein was administered. Blood samples were collected at precisely 1, 2, 3, 6 and 9 hours after the first blood sample was drawn. A washout period of 2 weeks was instituted between each experiment.

Interventions

Figure 1C:
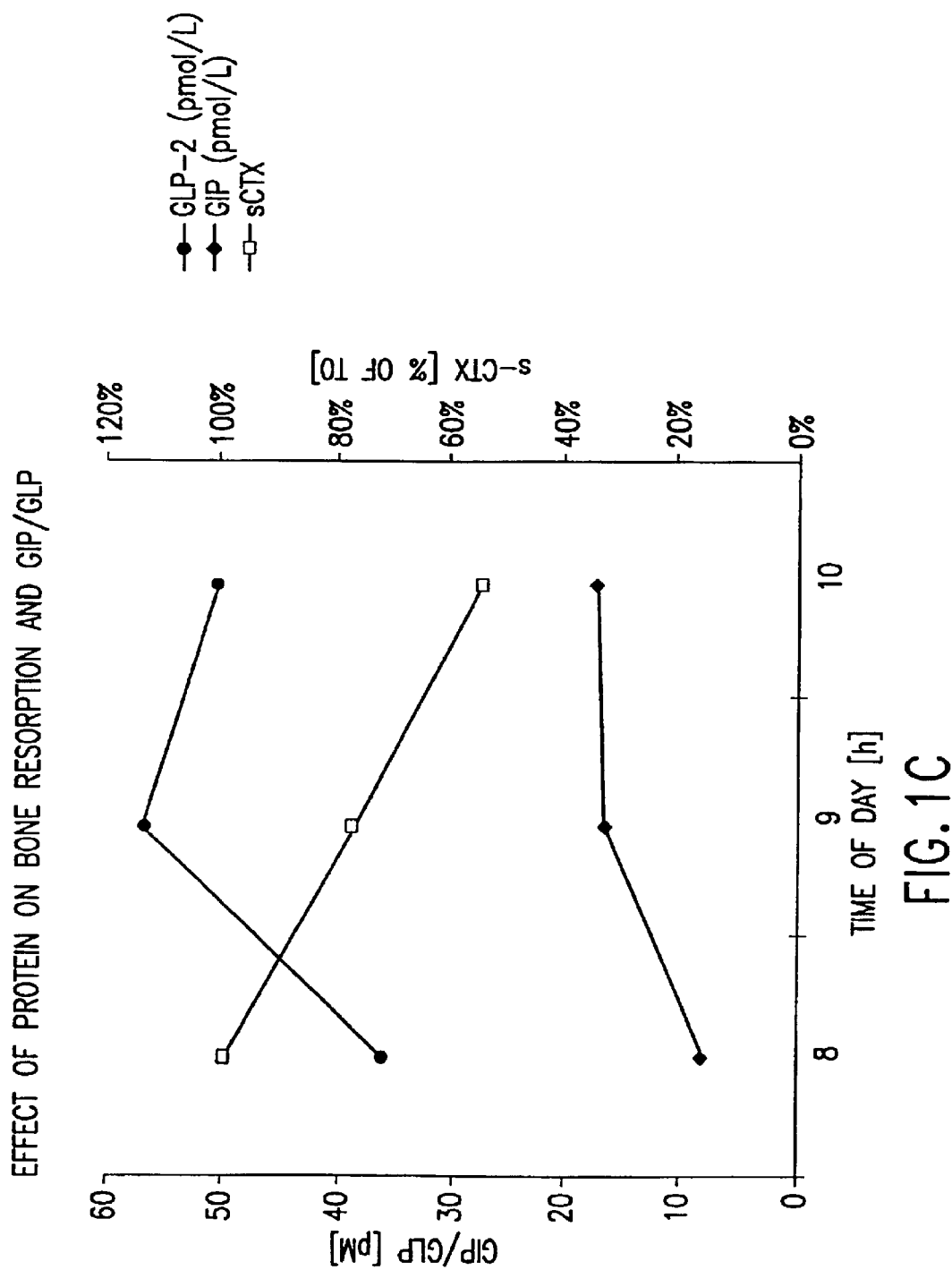

Oral protein consisted of 40 g protein powder (Casilan) dissolved in 600 ml water. Oral protein induced a reduction of 45% in S-CTX after 2 hours (FIG. 1C) whereas the occurrence of GLP-2 and GIP were both increased. The level of GIP increased from 8 pM to 17 pM and the level of GLP-2 increased from 36 pM to 57 pM after 1 hour decreasing slightly after 2 hours to the level of 51 pM. These results indicate that increasing concentrations of GLP-1 and/or GLP-2 can reduce bone resorption as measured by S-CTX.

Example 4

Effect of a Normal Mixed Meal on GLP-1, GLP-2, and Bone Resorption Rate

Seven short-bowel patients (<140 cm remnant small bowel) were recruited. Four females and three males were studied comparing the effects of a normal mixed meal on GLP-1, on GLP-2 and on bone turnover. Bone turnover was assayed by measuring the amount of S-CTX in a subject's serum. Briefly, an imunoassay was performed using monoclonal antibodies specific to S-CTX fragments generated exclusively from collagen type I degradation during resorption of mature bone tissue (Rosenquist et al., 1998, Clin. Chem. 44:2281–2289). The methodology of the measurement of GLP-1 and GLP-2 and the description of the test subjects were as described in detail in Jeppesen et al. (2000, "Elevated plasma glucagon-like peptide 1 and 2 concentrations in ileun resected short bowel patients with a preserved colon", Gut 47: 370–376).

Sampling

Subjects fasted overnight and initial peripheral venous blood was collected 15 minutes prior to the test meal. The test meal was completed in 15 minutes. Venous blood was collected at 10, 20, 30, 45, 60, 120 and 180 minutes after the start of the test meal.

Interventions

The normal mixed meal consisted of rye bread, toast, butter, cheese, jam, yogurt, banana, and orange juice (total weight 755 g), with an energy content of 3.92 MJ and a protein:carbohydrate:fat energy ratio of 10%:52%:37% evaluated from food tables.

Figure 2:
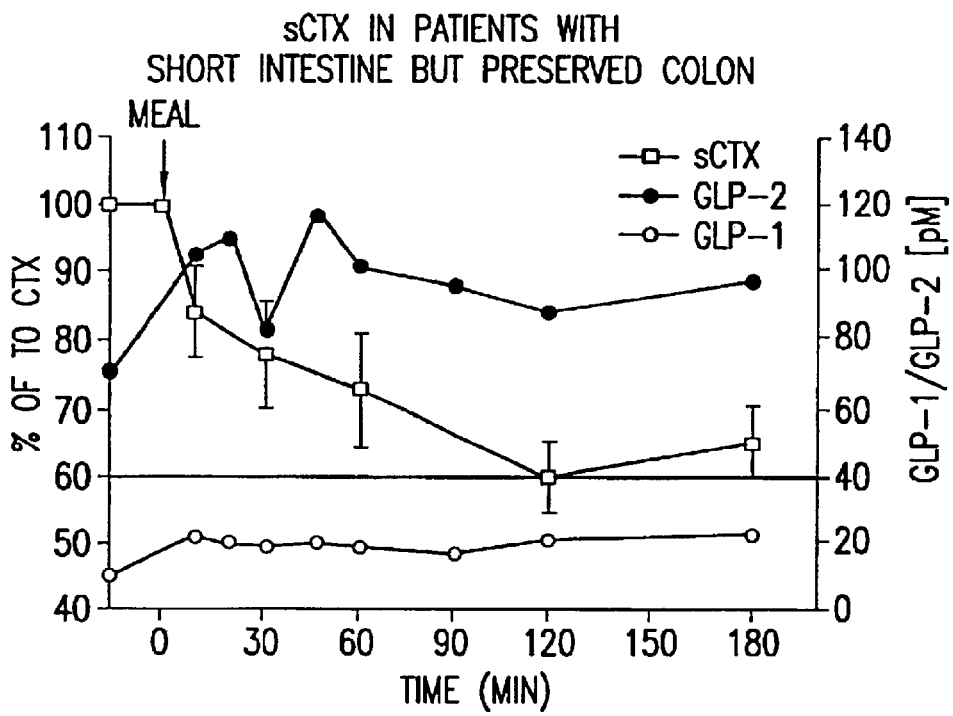
FIG. 2 shows the levels of GLP-1, GLP-2, and S-CTX over a 3 hour period following a normal meal. Subjects had a short intestine with a preserved colon.

A normal mixed meal induced a reduction of 40% in S-CTX after 2 hours (FIG. 2) whereas GLP-1 and GLP-2 levels were both increased. The level of GLP-1 was increased from 70 pM to 98 pM after 3 hours and the level of GLP-2 was increased from 10 pM to 22 pM after 3 hours. These results indicate that increasing levels of GLP-1 and/or GLP-2 can reduce bone resorption as measured by S-CTX.

Example 5

Effect of a GLP-2 Injection on GLP-2 and Bone Resorption Rate

Six healthy women and 3 healthy men between the ages of 24–53 were included in a study comparing the effect of a GLP-2 injection on GLP-2 expression levels and on bone turnover. Bone turnover was assayed by measuring the amount of S-CTX in a subject's serun. Briefly, an imunoassay was performed using monoclonal antibodies specific to S-CTX fragments generated exclusively from collagen type I degradation during resorption of mature bone tissue (Rosenquist et al., 1998, Clin. Chem. 44:2281–2289). The description of the methodology of measurement of full length GLP-2 and total GLP-2 (including degradation products by, e.g., DPP IV protease) and the description of the test persons was as described in detail in Hartmann et al. (2000, "In vivo and in vitro degradation of glucagon-like peptide-2 in humans", J. Clin. Endocrinol. Metab. 85:2884–2888).

Sampling

Blood samples were drawn at regular intervals before, during, and after the injection.

Interventions

Figure 3:
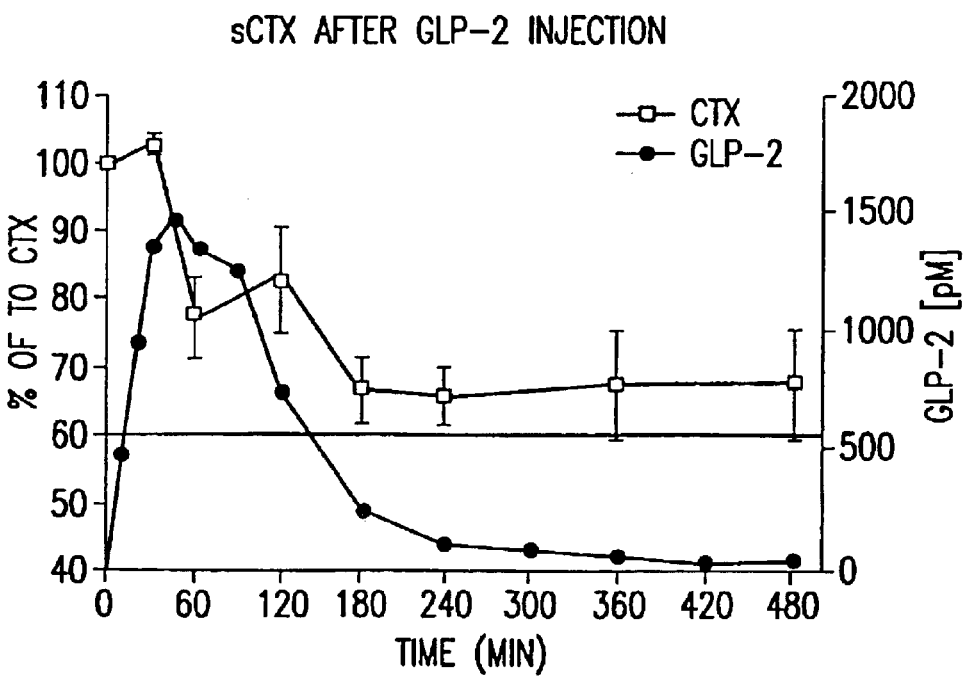
FIG. 3 shows the levels of S-CTX and GLP-2 over a 7 hour period following a subcutaneous bolus injection of 400 pg of synthetic human GLP-2.

The test subjects received a subcutaneous bolus injection of 400 pg synthetic human GLP-2. The GLP-2 injection induced a reduction of 35% in S-CTX after 3 hours, whereas the level of GLP-2 increased naturally after the injection to a peak after 1 hour indicating that an increase in GLP-2 results in the reduction of bone resorption as measured by the S-CTX immunoassay (FIG. 3).

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

What is claimed is:

1. A pharmaceutical composition comprising an effective amount of:
   (a) a GLP-2; and
   (b) another therapeutic agent which is an anti-osteoporosis agent.

2. A pharmaceutical composition comprising an effective amount of:
   (a) a GLP-2; and
   (b) another therapeutic agent which is an anti-osteoporosis agent, wherein the anti-osteoporosis agent is alendronate sodium, clodronate, etidronate, gallium nitrate, mithramycin, norethindrone acetate, pamidronate, or risedronate sodium.

3. The pharmaceutical composition of any one of claim 1 or 2, wherein the composition further comprises a pharmaceutically acceptable carrier.

* * * * *